(12) United States Patent  
Haakonsen et al.

(10) Patent No.: US 6,747,672 B1  
(45) Date of Patent: Jun. 8, 2004

(54) VIRTUAL PATIENT HOT SPOTS

(75) Inventors: Karl Haakonsen, Roslindale, MA (US); Bryan Bergeron, Brookline, MA (US); Stas Taraschansky, Natick, MA (US); Raymond C. Kurzweil, Newton, MA (US)

(73) Assignee: Medical Learning Company, Inc., Wellesley Hills, MA (US)

( * ) Notice: Subject to any disclaimer, the term of this patent is extended or adjusted under 35 U.S.C. 154(b) by 302 days.

(21) Appl. No.: 09/603,368

(22) Filed: Jun. 26, 2000

Related U.S. Application Data

(60) Provisional application No. 60/162,876, filed on Nov. 1, 1999.

(51) Int. Cl.[7] .................................................. G09G 5/00
(52) U.S. Cl. .................... 345/700; 345/716; 345/764; 345/771; 434/262
(58) Field of Search ............................... 345/700, 716, 345/727, 733, 764, 771, 810, 835, 839; 434/262, 266, 267, 269–271, 365; 703/13; 705/2, 3; 709/203, 217

(56) References Cited

U.S. PATENT DOCUMENTS

| | | | |
|---|---|---|---|
| 4,737,921 A | 4/1988 | Goldwasser et al. | |
| 4,907,973 A | 3/1990 | Hon | |
| 5,385,474 A | 1/1995 | Brindle | |
| 5,680,590 A | 10/1997 | Parti | |
| 5,769,640 A * | 6/1998 | Jacobus et al. | 434/262 |
| 5,791,907 A * | 8/1998 | Ramshaw et al. | 434/262 |
| 5,800,179 A | 9/1998 | Bailey | |
| 5,825,941 A | 10/1998 | Linford et al. | |
| 5,882,206 A | 3/1999 | Gillio | |
| 5,984,368 A * | 11/1999 | Cain | 283/115 |
| 6,050,826 A | 4/2000 | Christianson et al. | |
| 6,074,213 A | 6/2000 | Hon | |
| 6,077,082 A | 6/2000 | Gibson et al. | |
| 6,126,450 A * | 10/2000 | Mukai et al. | 434/262 |
| 6,167,362 A | 12/2000 | Brown et al. | |
| 6,246,975 B1 | 6/2001 | Rivonelli et al. | |
| 6,272,468 B1 * | 8/2001 | Melrose | 705/2 |
| 6,273,728 B1 | 8/2001 | Van Meurs et al. | |
| 6,289,299 B1 | 9/2001 | Daniel, Jr. et al. | |
| 6,307,567 B1 | 10/2001 | Cohen-Or | |
| 6,369,812 B1 | 4/2002 | Iyriboz et al. | |
| 6,425,764 B1 * | 7/2002 | Lamson | 434/236 |
| 6,527,558 B1 * | 3/2003 | Eggert et al. | 434/262 |
| 2001/0041992 A1 * | 11/2001 | Lewis et al. | 705/3 |

* cited by examiner

*Primary Examiner*—Sy D. Luu  
(74) *Attorney, Agent, or Firm*—Fish & Richardson P.C.

(57) ABSTRACT

A method of simulating an encounter with a virtual patient includes displaying an image of the virtual patient, receiving user selection of an area of the image of the virtual patient, and transmitting signals that associated with the user selected area of the image, the signals being based on the state of the virtual patient.

10 Claims, 30 Drawing Sheets

1502 {
- Object Model Key "Patient Views"
- Object Model MMFile1 "Body Renderings\MorphMan\aprime.jpg"
- Object Model MMFile2 "Body Renderings\MorphMan\bprime.jpg"
- Object Model MMFile3 "Body Renderings\MorphMan\cprime.jpg"
- Object Model MMFile4 "Body Renderings\MorphMan\dprime.jpg"

1504 {
- Object Model Key "ROS Head"
- Object Model MMFile1 "Body Renderings\MFaces\Neutral.jpg"

1506 {
- Object ABD Key "Front Auscultation"
- Object ABD MMFile "Body Renderings\New_Male_Fat\FatChBkMAus.jpg"
- Object ABD Sound1 "Wav Files\Other\Bowel1.wav"
- Object ABD Sound2 "Wav Files\Other\Bowel2.wav"
- Object ABD Sound3 "Wav Files\Other\Bowel3.wav"
- Object ABD Sound4 "Wav Files\Other\Bowel2.wav"

1508 {
- Object ABD Key "Front Percussion"
- Object ABD MMFile "Body Renderings\New_Male_Fat\FatChBkMPercuss.jpg"
- Object ABD Sound1 "Wav Files\Percussion\PercusDull.wav"
- Object ABD Sound2 "Wav Files\Percussion\PercusDull.wav"
- Object ABD Sound3 "Wav Files\Percussion\PercusFlat.wav"
- Object ABD Sound4 "Wav Files\Percussion\PercusFlat.wav"
- Object ABD Sound5 "Wav Files\Percussion\PercusResonant.wav"
- Object ABD Sound6 "Wav Files\Percussion\PercusResonant.wav"
- Object ABD Sound7 "Wav Files\Percussion\PercusDull.wav"
- Object ABD Sound8 "Wav Files\Percussion\Exclame.wav"

FIG. 15A-1

```
Object Chest Key      "Front Auscultation"
Object Chest MMFile   "Body Renderings\New_Male_FatFatChBkMAus.jpg"
Object Chest Sound1   "Wav Files\Heart Sounds\Normal (A).wav"
Object Chest Sound2   "Wav Files\Heart Sounds\Normal (P).wav"
Object Chest Sound3   "Wav Files\Heart Sounds\Normal (T).wav"
Object Chest Sound4   "Wav Files\Heart Sounds\Normal (M).wav"
```
⎫  
⎬ 1510  
⎭

```
Object Chest Key      "Back Auscultation"
Object Chest MMFile   "Body Renderings\New_Male_FatFatChBkMAus.jpg"
Object Chest Sound1   "Wav Files\Breath Sounds\NormBSApex.wav"
Object Chest Sound2   "Wav Files\Breath Sounds\NormBSApex.wav"
Object Chest Sound3   "Wav Files\Breath Sounds\NormBSBase.wav"
Object Chest Sound4   "Wav Files\Breath Sounds\NormBSBase.wav"
Object Chest Sound5   "Wav Files\Breath Sounds\NormBSBase.wav"
Object Chest Sound6   "Wav Files\Breath Sounds\NormBSBase.wav"
```
⎫  
⎬ 1512  
⎭

```
Object Chest Key      "Back Percussion"
Object Chest MMFile   "Body Renderings\New_Male_FatChBkMPercuss.jpg"
Object Chest Sound1   "Wav Files\Percussion\PercusResonant.wav"
Object Chest Sound2   "Wav Files\Percussion\PercusResonant.wav"
Object Chest Sound3   "Wav Files\Percussion\PercusResonant.wav"
Object Chest Sound4   "Wav Files\Percussion\PercusResonant.wav"
Object Chest Sound5   "Wav Files\Percussion\PercusResonant.wav"
Object Chest Sound6   "Wav Files\Percussion\PercusResonant.wav"
Object Chest Sound7   "Wav Files\Percussion\PercusFlat.wav"
Object Chest Sound8   "Wav Files\Percussion\PercusFlat.wav"
```
⎫  
⎬ 1514  
⎭

FIG. 15A-2

1516 {
- Object CV Key     "EKG"
- Object CV MMFile1 "EKGs\Normsinr.jpg"
- Object CV Entry   "Normal sinus rhythm with no signs of past or current cardiac events."

1518 {
- Object Ext Key     "Extremities - Left Hand"
- Object Ext MMFile1 "Extrem\MNLHand.jpg"
- Object Ext Entry   "Left hand normal to inspection."

1520 {
- Object Ext Key     "Extremities - Right Hand"
- Object Ext MMFile1 "Extrem\MNRHand.jpg"
- Object Ext Entry   "Right hand normal to inspection."

FIG. 15A-3

1522 {
- Object Ext Key    "Extremities - Feet"
- Object Ext MMFile1    "Extrem\MNFeet.jpg"
- Object Ext Entry    "Feet normal to inspection."

1524 {
- Object Heent Key    "Eyes Exam"
- Object Heent MMFile1    "Pupils\NormEyes.jpg"
- Object Heent Entry    "Pupils equal, round, and reactive to light."
- Object Heent Description    "Pupils equal, round, and reactive to light."

1526 {
- Object Heent Key    "Retinal Exam"
- Object Heent MMFile1    "Eye Exam\MorphRetSmall\a.jpg"
- Object Heent Entry    "Normal retinal exam."
- Object Heent Description    "Retinal Exam."

1528 {
- Object Heent Key    "Tympanic Membranes"
- Object Heent MMFile1    "Ear Exam\NormalEarBi.jpg"
- Object Heent Entry    "Tympanic membranes intact, no signs of fluid bilaterally."
- Object Heent Description    ""

1530 {
- Object Heent Key    "Throat Exam"
- Object Heent MMFile1    "Throat\M_Throat_hu.jpg"
- Object Heent Entry    "Throat is free of lesions"
- Object Heent Description    "No lesions, tongue midline, no active carries, mild peridontal disease."

FIG. 15B-1

1532 {
Object Neuro Key "Speech Pattern"
Object Neuro MMFile1 "Wav Files\speech\MspeechN.wav"
Object Neuro Entry "Normal speech pattern."
Object Neuro Description "Click button to hear speech"

1534 {
Object Neuro Key "Gait"
Object Neuro MMFile1 "Gait\MNGaitC.avi"
Object Neuro Entry "Normal gait."

1536 {
Object Rad Key "Chest Film"
Object Rad MMFile1 "CXRs\NormalMale.jpg"
Object Rad Entry "Chest film normal. Trachea midline. No interstitial opacities."

1538 {
Object Rad Key "Skull Film"
Object Rad MMFile1 "CXRs\NormalSkull.jpg"
Object Rad Entry "Skull film unremarkable. No masses or lesions visualized."

Evolution

1902 ⎰ Name "Diet & Exercise"
    ⎨ Number_Trigger_Events 1
    ⎨ Trigger_Type Action
    ⎱ Trigger_Index "Diet & Exercise"

1904 ⎰ Number_Initial_Inhibiting_Events 1
     ⎨ Initial_Inhibiting_Event_Type Evolution_Started
     ⎨ Initial_Inhibiting_Event_Index "Diet & Exercise"
     ⎱ Initial_Inhibiting_Event_Value 1

1906 ⎰ Interim_Mode_Time 4
     ⎱ Interim_Mode_Units Days

1908 ⎰ Number_Interim_Inhibiting_Events 0
     ⎱ Number_Evolutions_to_Cancel 0

Number_Evolving_Variables 4

1910a ⎰ Variable_to_Evolve "Vital_Weight"
      ⎨ Importance 4
      ⎨ Target_Multiple 0.90
      ⎨ Target_Increment 1
      ⎨ Target_Variance 1
      ⎨ Time 62
      ⎨ Time_Units Days
      ⎨ Time_Variance 2
      ⎨ Curve_Index 1
      ⎱ Evolve_Variance 2

FIG. 19A

1910b {
Variable_to_Evolve "Glucose, Fasting"
Importance 3
Target_Multiple 0.90
Target_Increment 1
Target_Variance 1.5
Time 52
Time_Units Days
Time_Variance 1
Curve_Index 1
Evolve_Variance 1.25

1910c {
Variable_to_Evolve "Glucose, Plasma"
Importance 5
Target_Multiple 0.95
Target_Increment 1
Target_Variance 1.25
Time 42
Time_Units Days
Time_Variance 1
Curve_Index 1
Evolve_Variance 1.45

1910d {
Variable_to_Evolve "Glucose, 2h Postprandial"
Importance 2
Target_Multiple 0.95
Target_Increment 1
Target_Variance 1.25
Time 42
Time_Units Days
Time_Variance 1
Curve_Index 1
Evolve_Variance 1.75

End_Evolution

FIG. 19B

```
2000 ─╮
      Migration
      Name        "ACT"
      Comment     "Activated clotting Time"
      Units       "s"
      Variable           "ACT"
      Start       143 ⎫
      Min         114 ⎬ 2002
      Max         186 ⎭
      Time_Step   1      ⎫
      Time_Unit   Minutes⎬ 2004
      Variance    0.4 } 2006
      Time_Jump   2
      End_Migration
```

```
Morph
Name      "vital_weightM"
Comment   "No Comment"
Variable  "vital_weight"
Min   164.0
Max   184.0
End_Morph
```

Object ROS Question   "Have you felt fatigued?"
Object ROS Answer   "Well, I do find myself more tired at the end of the day lately, even though my job hasn't changed in years."
Object ROS Keywords   "tire, fatigue, letharg"
Object ROS Entry   "Fatigued at the end of the day."
Object ROS MMFile1   "Body Renderings\FFaces\sullen.jpg"

Object Lab Test "Acetone"
Object Lab Description "No migration - Neg/Pos"
Object Lab Entry "Neg/Pos"

FIG. 27

Object Order Action "Acarbose"
Object Order Description "Oral Antidiabetic - Precose"
Object Order Entry "Given to patient PO; tolerated well"

FIG. 28

Object Physical Key "Oral Temperature"
Object Physical Text "Oral Temperature: $temperature$"

FIG. 29

COMPUTATION
Name            "Vital_BP_Diastolic"
Comment         "no comment"
Units           " mmHG"
Variable        "Vital_BP_Diastolic"
Method_Name "ComputeBPDiastolic"
Number_Arguments 1
Argument_Variable "Vital_BP_Systolic"
Variance     2
End_Computation

FIG. 30

VIRTUAL PATIENT HOT SPOTS

PRIORITY CLAIM

This application claims priority from co-pending provisional application Serial No. 60/162,876 filed on Nov. 1, 1999 which is incorporated by reference herein.

Reference to Related Applications

This application relates to the following applications U.S. Ser. No. 09/603,604, entitled "Web Simulator", filed Jun. 26, 2000; U.S. Ser. No. 09/603,045 entitled "Patient Simulator", filed Jun. 26, 2000; U.S. Ser. No. 09/603,422, entitled "Morphing", filed Jun. 26, 2000.

BACKGROUND

Desktop computer programs such as flight simulators, word-processors, and spreadsheets quickly respond to user input. Providing this kind of inter-activity over the Internet, however, has posed something of a challenge. This challenge stems, in part, from the simple communication model that describes most Internet traffic: clients (e.g., web-browsers) request pre-written web pages from servers, and the servers send the requested pages back for display.

Programmers have developed a number of different techniques to make web pages more inter-active. For example, some web pages include, or refer to, programs known as "applets." When a browser receives a web-page featuring an applet, the browser executes the applet instructions, for example, to receive user input, change a browser GUI (Graphical User Interface) display, and communicate with the server providing the web-page. Some applets, however, include a large number of instructions and can require a significant amount of time to travel over the Internet to a user's browser.

Another technique for making web pages more responsive to users involves dynamic generation of web pages by servers. For example, PHP (Personal Home Page), ASP (Active Server Page), and CGI (Common Gateway Interface) scripts can dynamically produce a web page based on script instructions and variables. Script processing, however, adds yet another task to web-servers faced with handling large bursts of browser requests for information.

SUMMARY

In an aspect, the invention features a method of simulating an encounter with a virtual patient including displaying an image of the virtual patient, receiving user selection of an area of the image of the virtual patient, and transmitting signals that associated with the user selected area of the image, the signals being based on the state of the virtual patient.

Advantages of the invention will become apparent in view of the following description, including the figures, and the claims.

The details of one or more embodiments of the invention are set forth in the accompanying drawings and the description below. Other features, objects, and advantages of the invention will be apparent from the description and drawings, and from the claims.

DESCRIPTION OF DRAWINGS

Brief Description of the Drawings

FIGS. 1 to 5 are diagrams illustrating a network application architecture.

Figure 6:
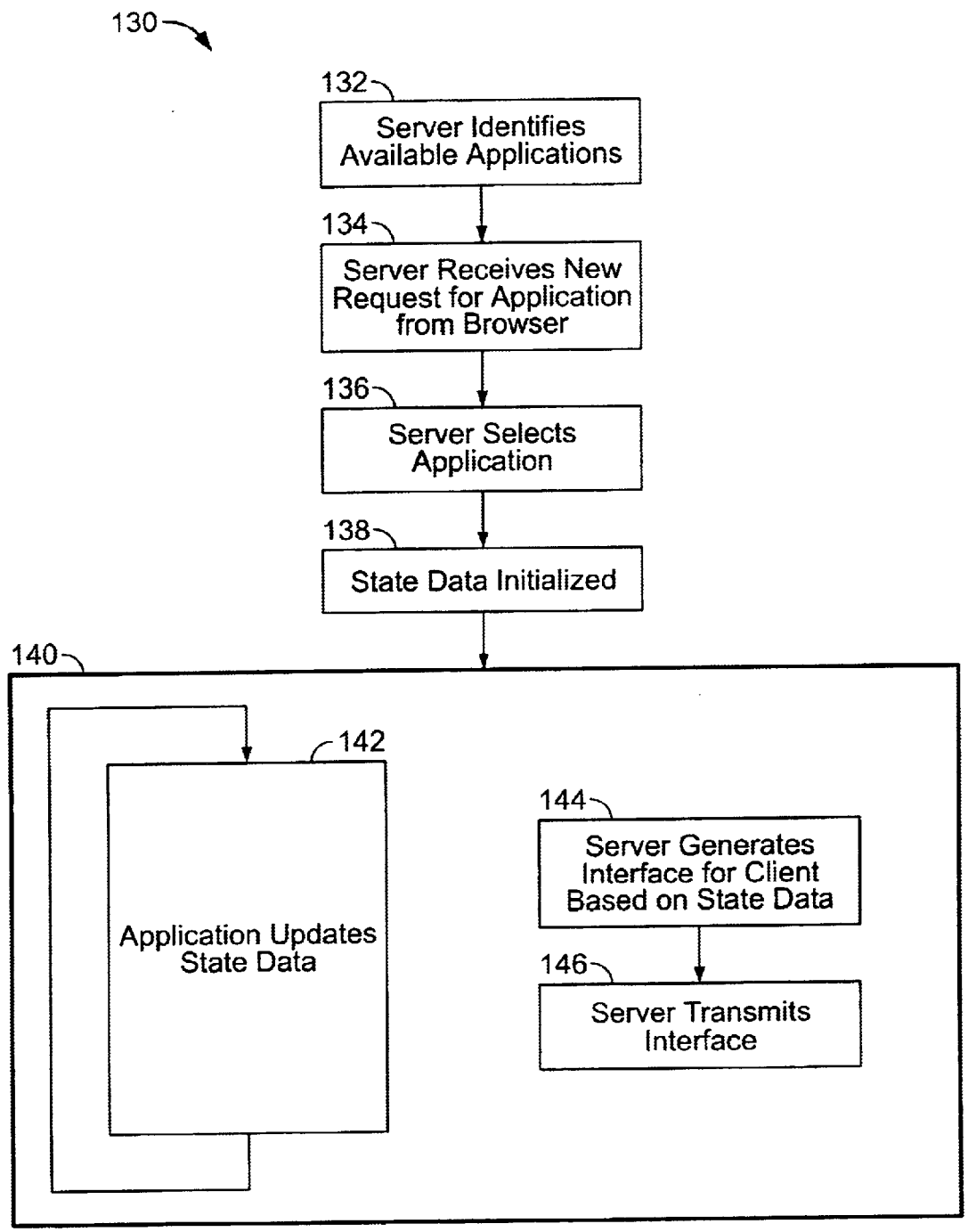

FIG. 6 is a flowchart of a server process for providing an application to different network users.

Figure 7:
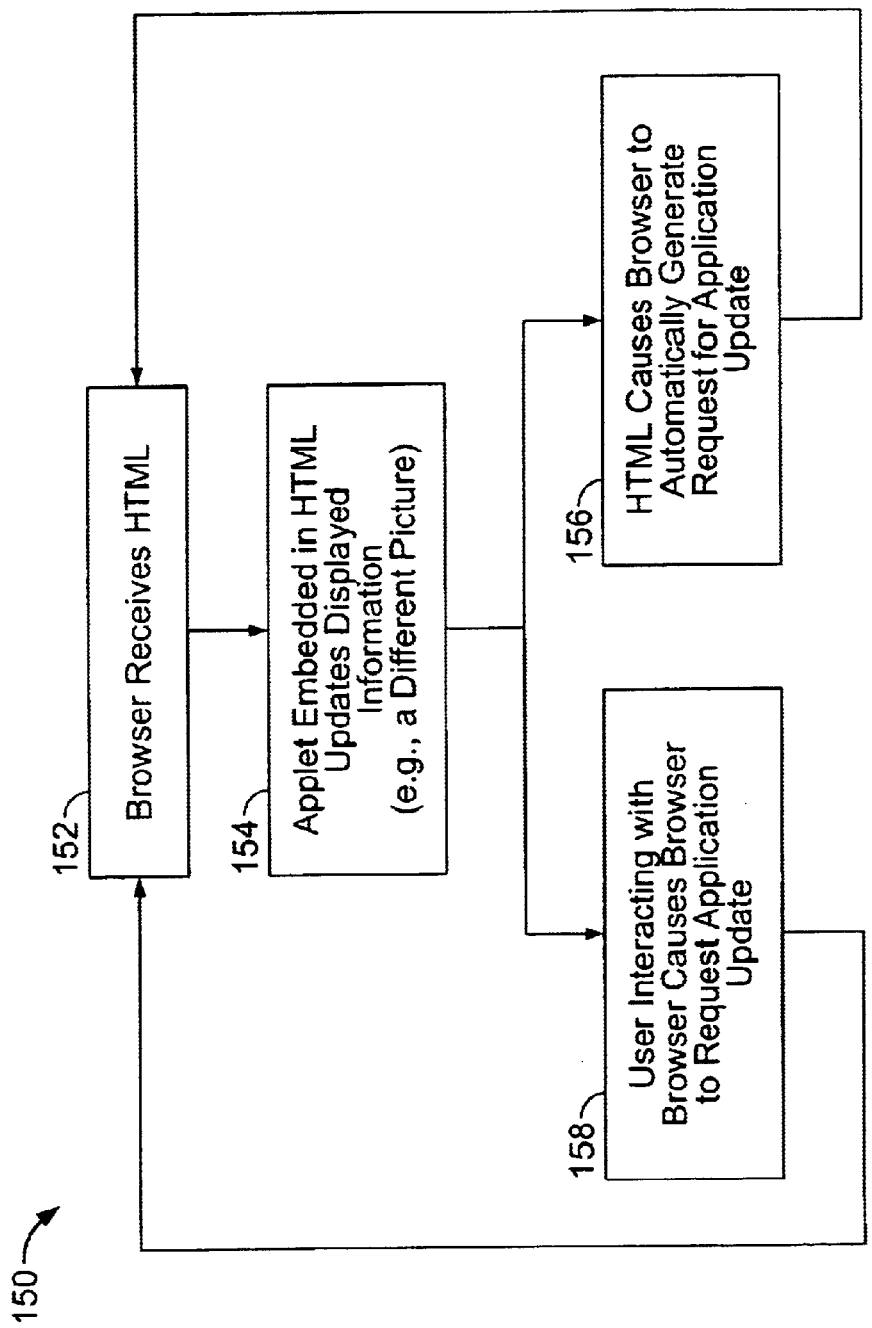

FIG. 7 is a flowchart of a client process for presenting a user interface to network users.

FIGS. 8–14 are screenshots of a user interface that presents a virtual patient.

FIGS. 15A and 15B are listings of statements associating multimedia files with different virtual patient characteristics.

Figure 16:
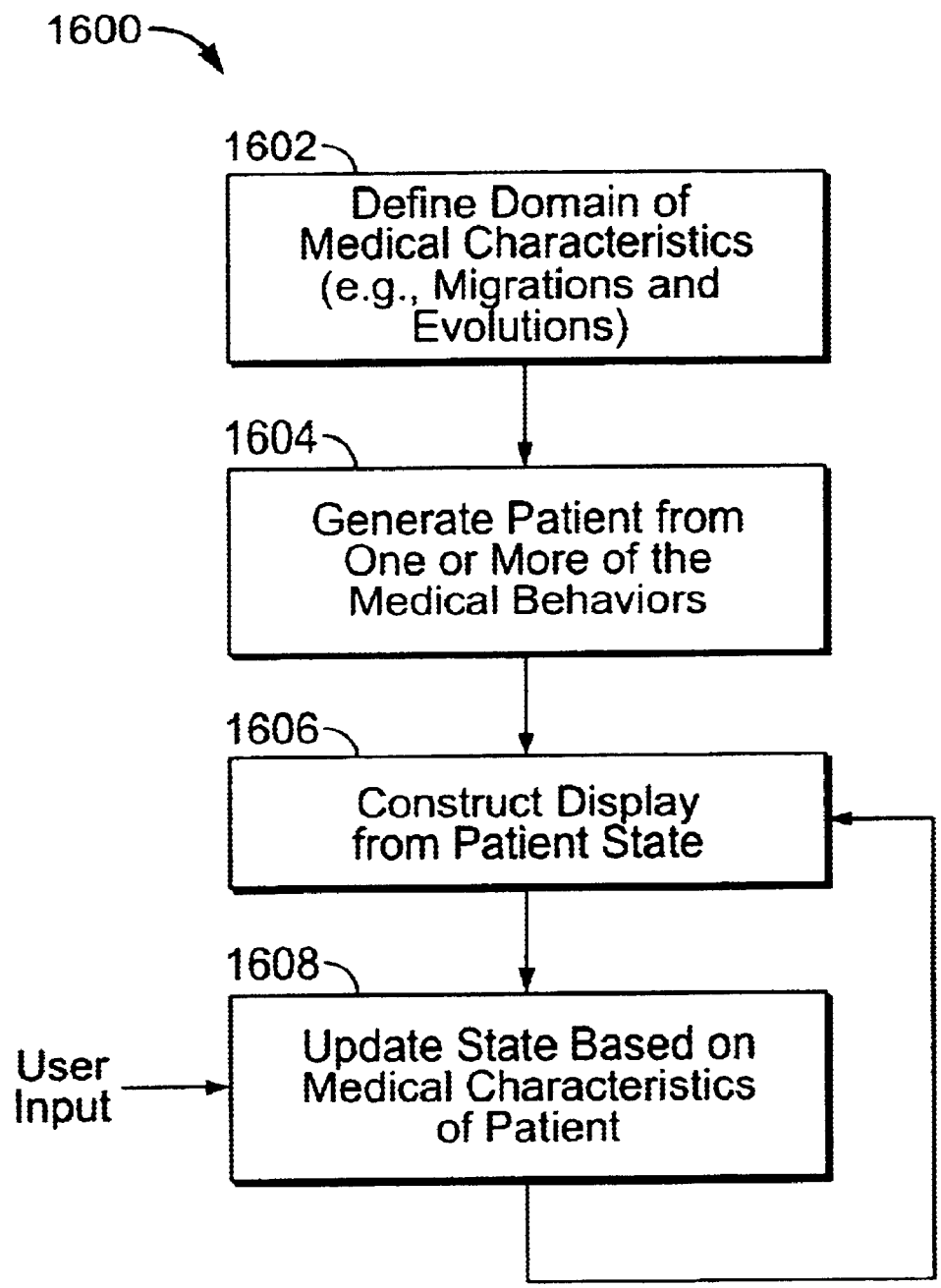

FIG. 16 is a flowchart of a process for providing a virtual patient.

Figure 17:
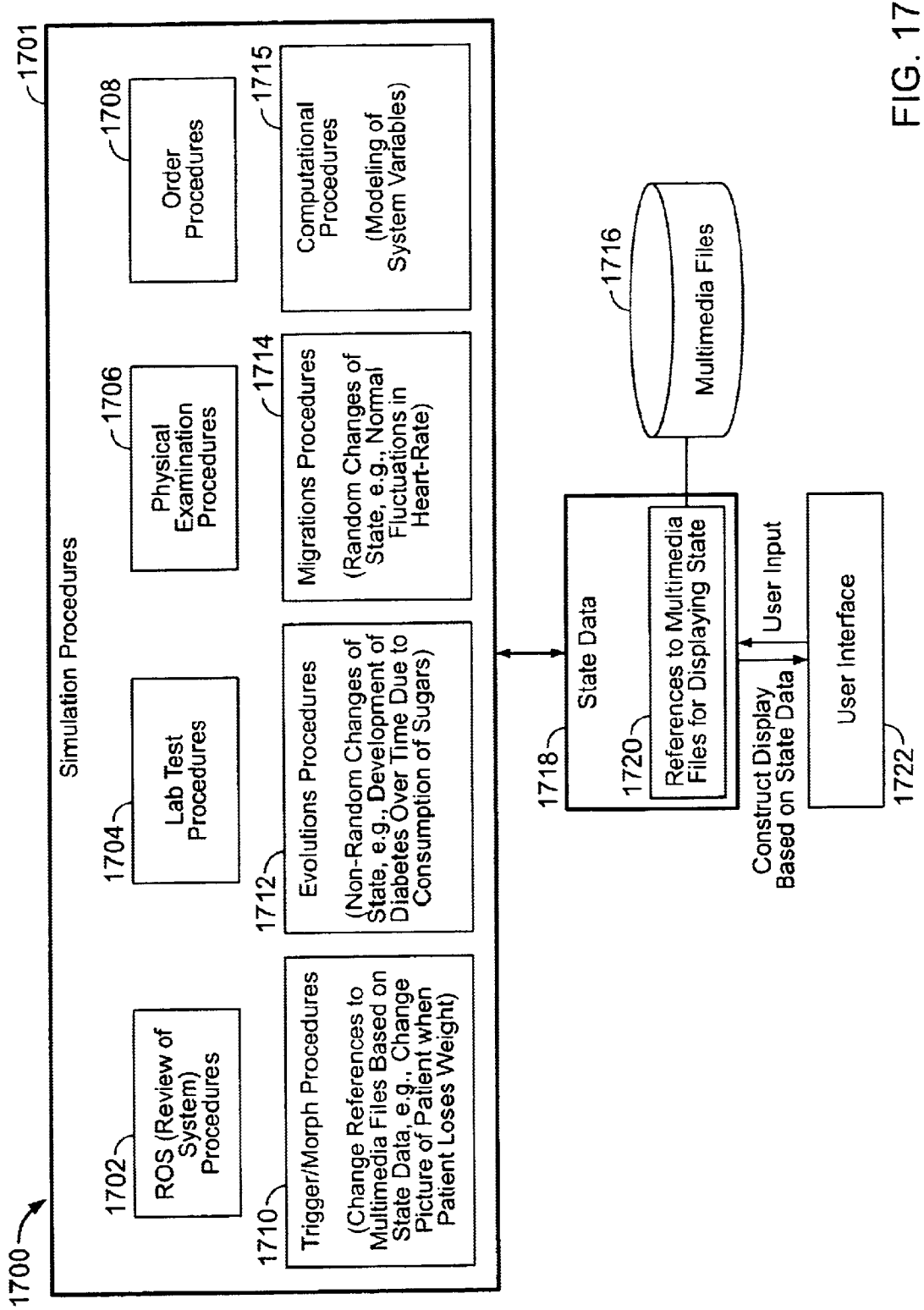

FIG. 17 is a diagram of a virtual patient simulator.

Figure 18:
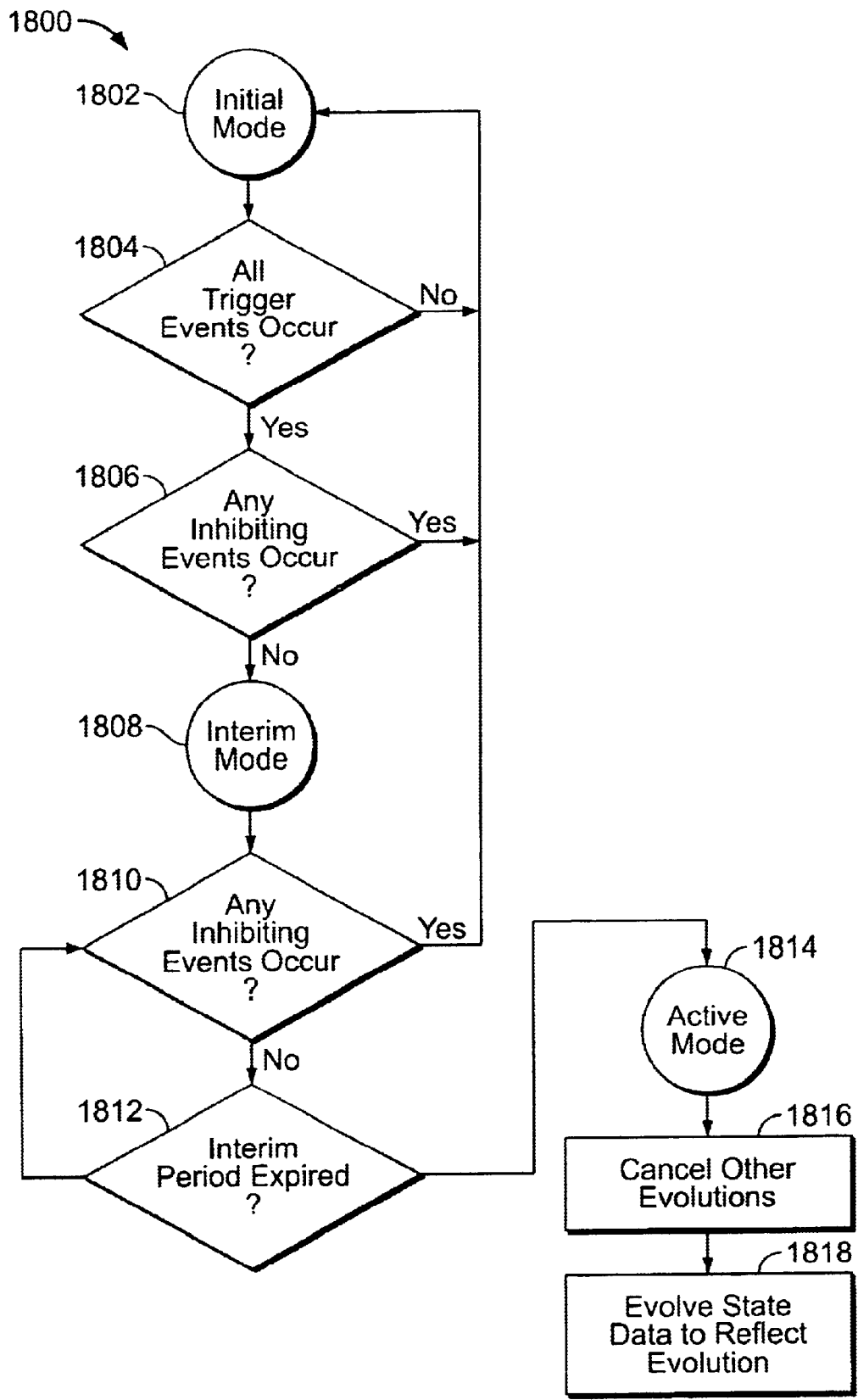

FIG. 18 is a flowchart of a process for evolving a medical condition.

FIG. 19 is a listing of statements defining an evolution.

Figures 20, 21:
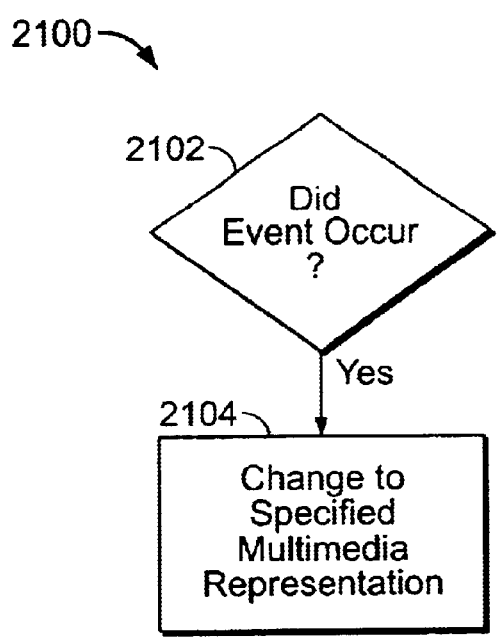

FIG. 20 is a listing of statements defining a migration.

FIG. 21 is a flowchart of a process for changing multimedia presentations associated with a virtual patient.

Figure 22:
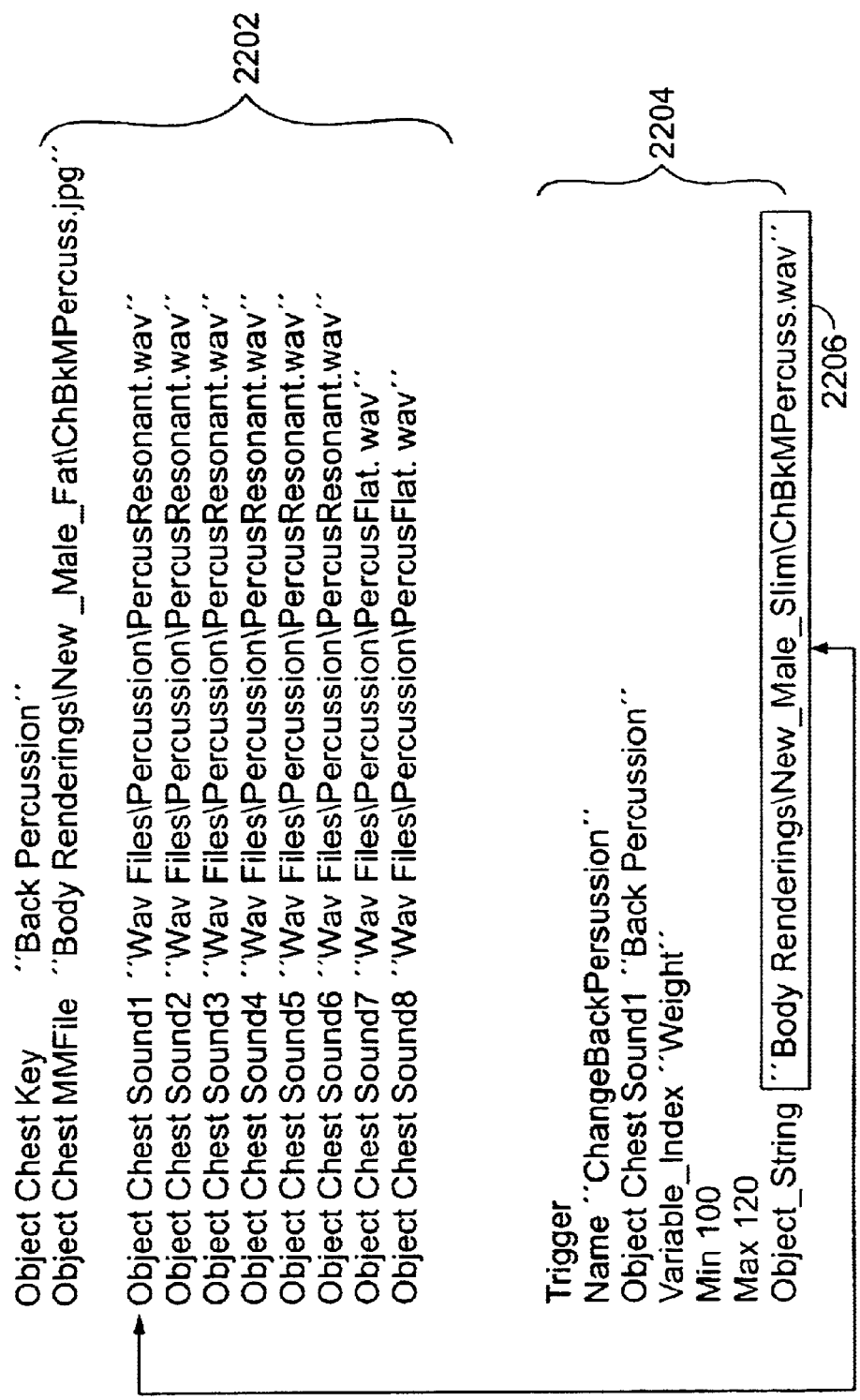

FIG. 22 is a diagram illustrating a change of a multimedia presentation associated with a virtual patient.

Figures 23, 24:
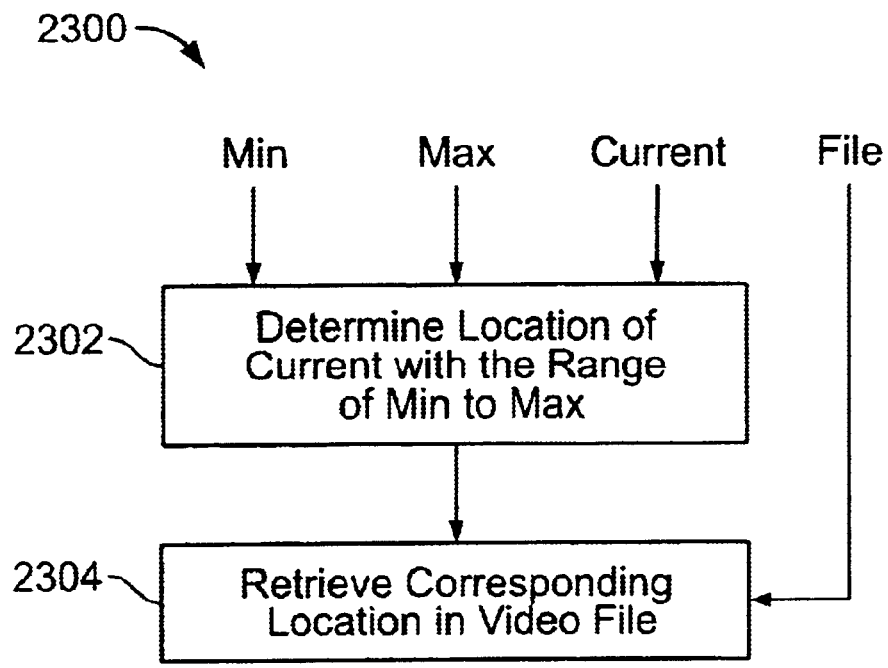

FIG. 23 is a flowchart of a process for morphing a virtual patient.

FIG. 24 is a listing of statements defining a morphing operation.

Figures 25, 26:
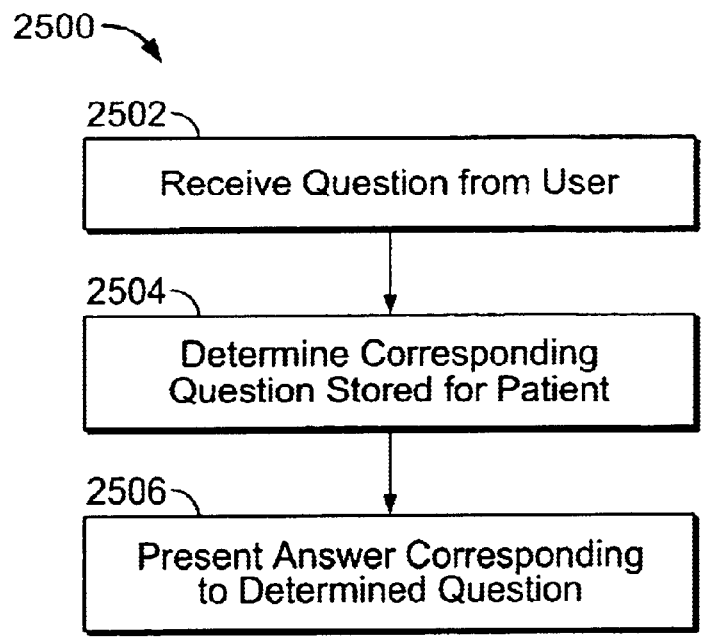

FIG. 25 is a flowchart of a process for providing virtual patient responses to questions.

FIG. 26 is a listing of statements defining virtual patient answers to questions.

FIG. 27 is a listing of statements defining a response to a lab test.

FIG. 28 is a listing of statements defining an action.

FIG. 29 is a listing of statements defining a response to physical examination.

FIG. 30 is a listing of statements defining a computation.

Figure 31:
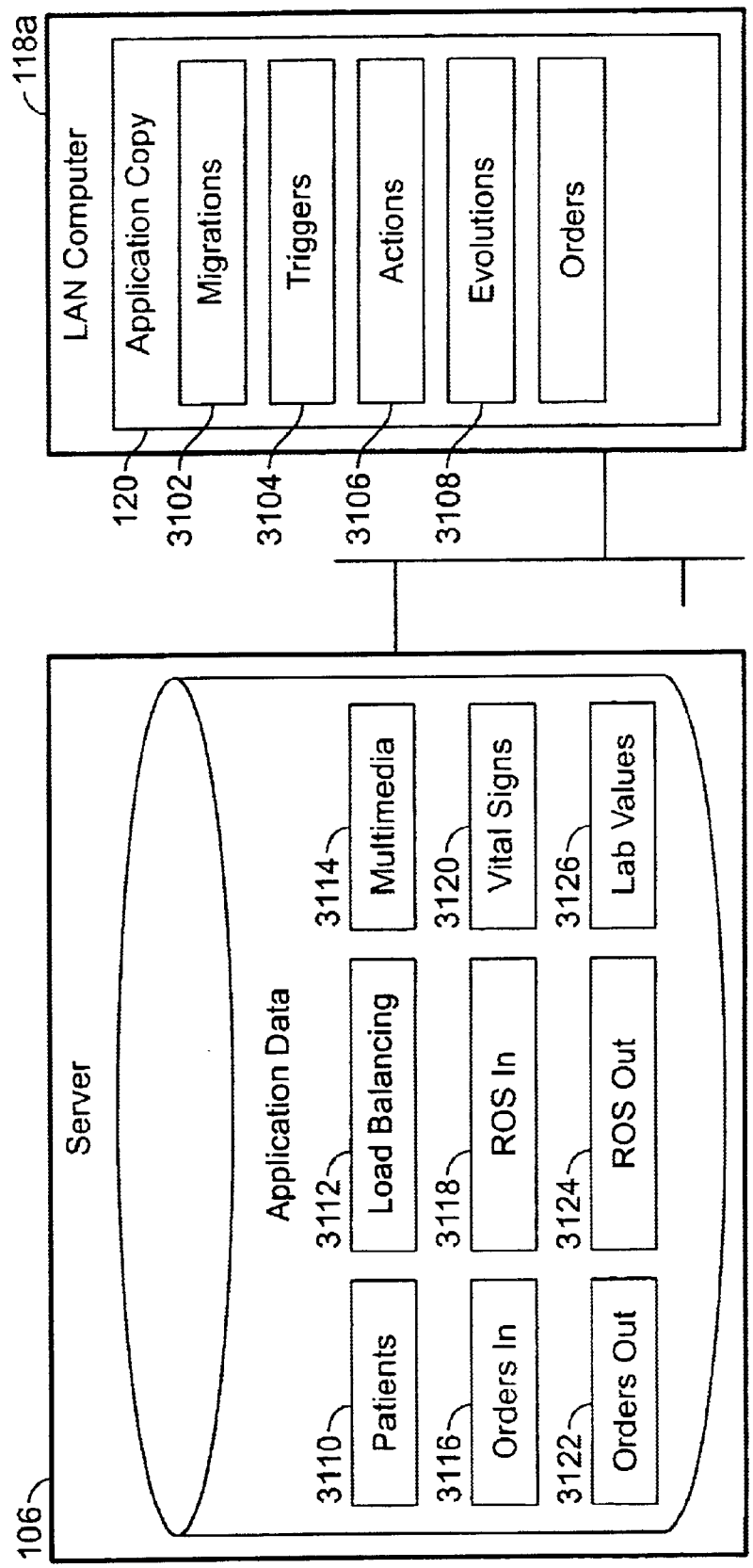

FIG. 31 is a diagram of a virtual patient simulator using the network application architecture.

Like reference symbols in the various drawings indicate like elements.

DETAILED DESCRIPTION

I. Network Architecture

A. Introduction

Figure 1:
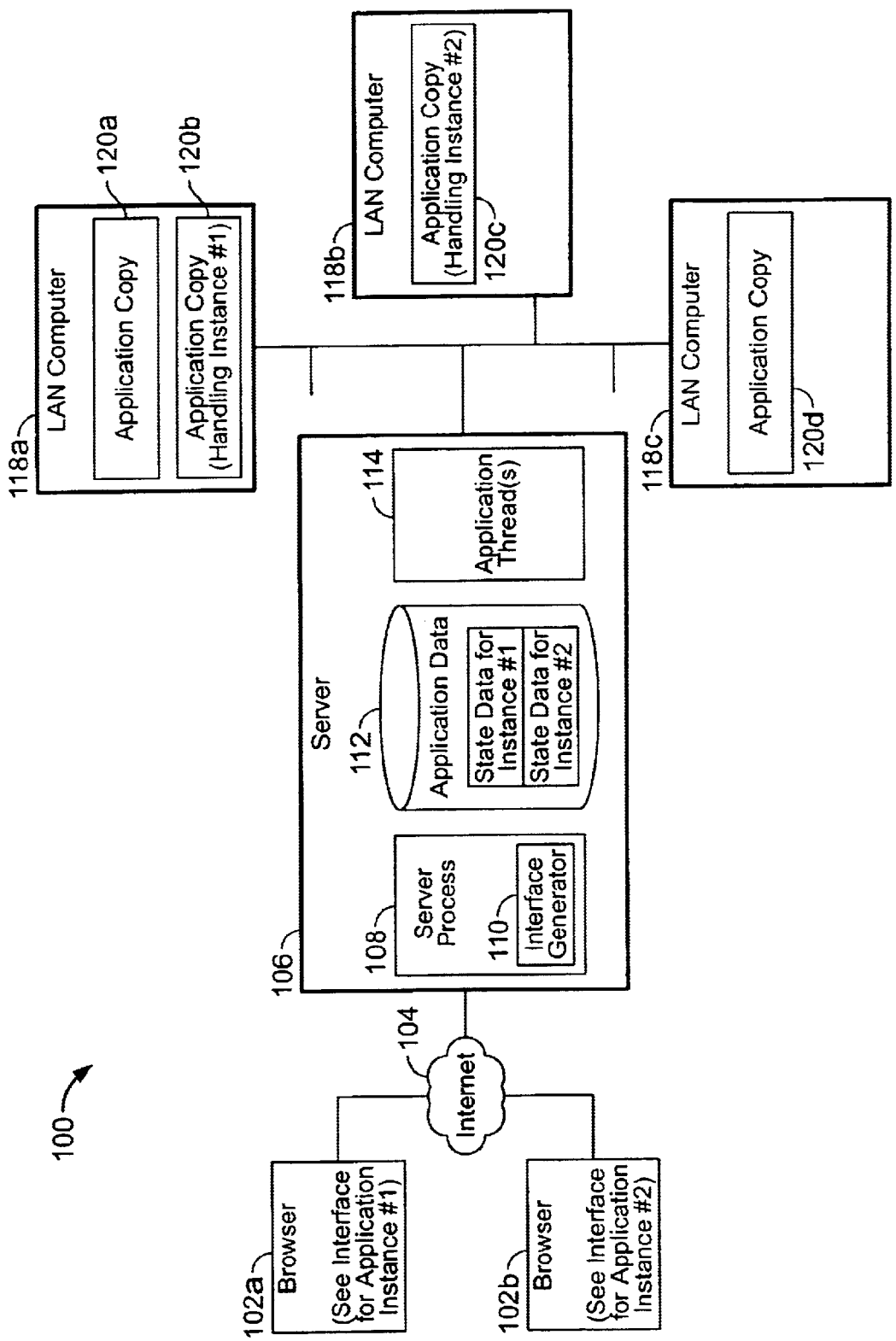

FIG. 1 shows a system 100 that uses the Internet 104 as a vehicle for providing complex, interactive applications to a large number of network users operating ordinary web-browsers 102a, 102b (e.g., Microsoft™ Internet Explorer™). The architecture 100 provides each user with a different "instance" of the application. That is, each user perceives an application program responsive to that user's input, much like an ordinary program residing on the user's personal computer. In the scheme shown in FIG. 1, the web-browsers 102a–102b need not receive the actual application instructions, but instead receive interface instructions for constructing a browser display and presenting different user interface controls. The interfaces are like application facades with the real application instructions residing on a remote system.

As shown in FIG. 1, the system 100 includes a network server 106 that stores the "state" 112 of each application instance. State data 112 can include the current values of different variables used by an application. A single application can handle more than one "instance." For example, an application can read an instance's state data 112, perform some processing, update and store the instance's state data 112, and move on to another instance's state data.

Conceptually, state data 112 represents the intersection between local area network computers 118a–118c running different copies of an application 120a–120d and a process 108 that dynamically constructs web pages for each application instance. Applications 120a–120d continually operate and update the state data 112. Independently, the server 106 can process user input and prepare browser instructions (e.g., HTML (Hypertext Markup Language)) for each instance.

For example, in one embodiment, the applications 120a–120d provide users with a simulation of a patient medical exam (i.e., simulation of a medical exam to a "virtual" patient). The simulation enables network users to interact with web-page controls (e.g., buttons, icons, and text fields) to examine, diagnose, and attempt to return a virtual patient to health. For this application, the state data 112 can include a virtual patient's vital signs (e.g., heart rate, pulse, and weight), images or references to images of the virtual patient's current appearance, medical orders and queries received from the user, and other information. The medical simulation applications 120a–120d continually update the state data 112 for a patient to reflect the virtual patient's health. For example, the medical simulation applications 120a–120d may slowly decrease a virtual patient's weight over time when a user prescribes a diet. While the medical simulation applications 120a–120d run behind the scenes, an interface generator 110 uses the state data 112 to construct browser instructions that display an appearance of the user's virtual patient and provide information (e.g., a medical history) requested by the user.

The network system of FIG. 1 can handle the large numbers of users that typically visit popular web sites. For example, pooling the computational resources of the LAN computers 118a–118c enables the system 100 to support a large number of application instances. Additionally, the system 100 enables a network administrator to add computers to a local area network to further increase system "horse-power". Additionally, the server 106 does not need to deliver copies of the application 120a–120d to each network user. This can reduce network traffic. Keeping the application instructions on local area network machines also enables a site manager to easily replace and modify the applications, for example, to fix bugs or provide new features. This also prevents users from easily copying the programs. The system 100 also separates interface generation (server 106) from the actual "number crunching" (i.e., execution) of the application 120a–120d. This separation enables the server 106 to easily customize each user's interface. For example, more sophisticated computers or computers featuring faster network connections can receive interface instructions for more elaborate multimedia presentations.

B. Illustration of Operation

Figure 2:
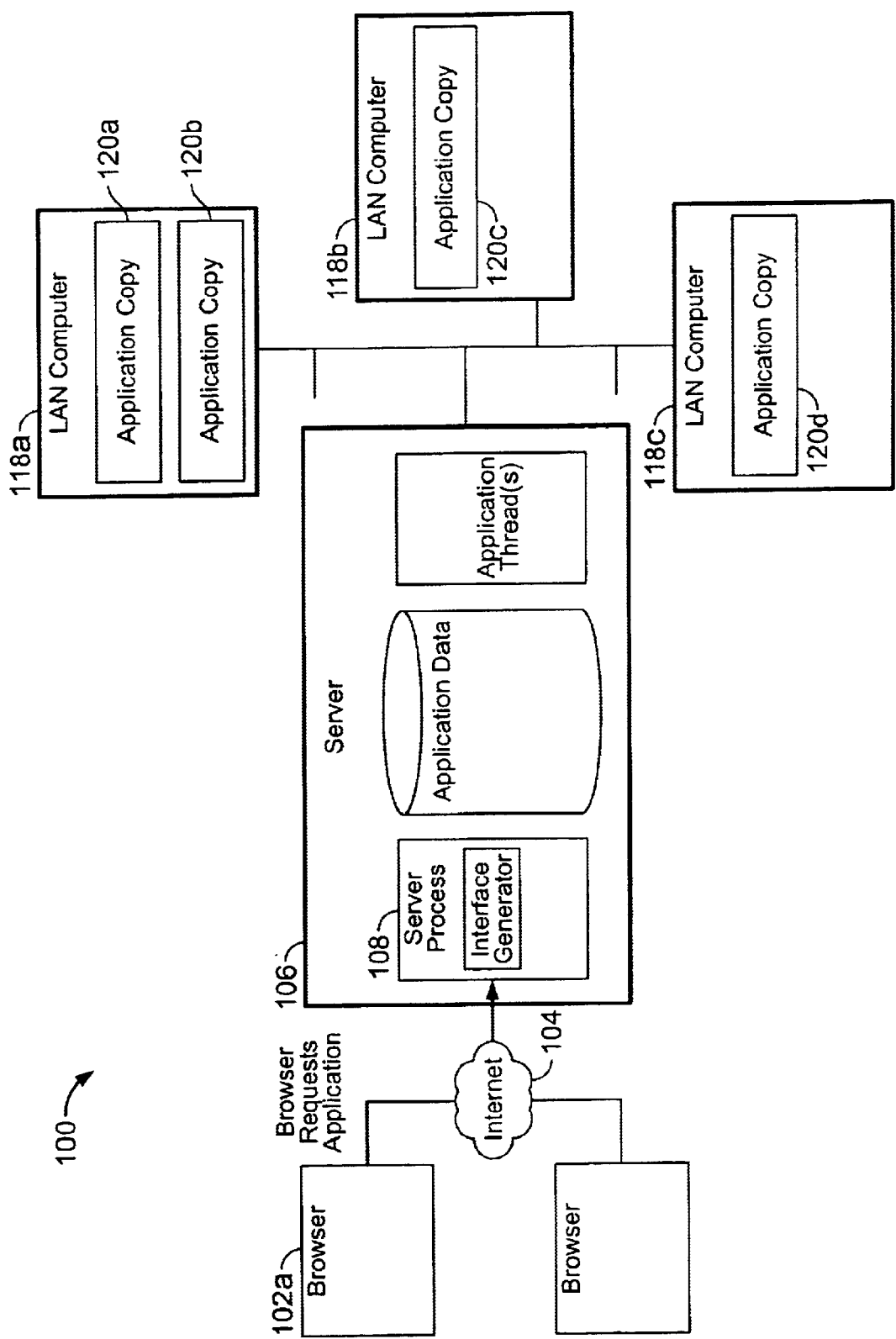
Figure 3:
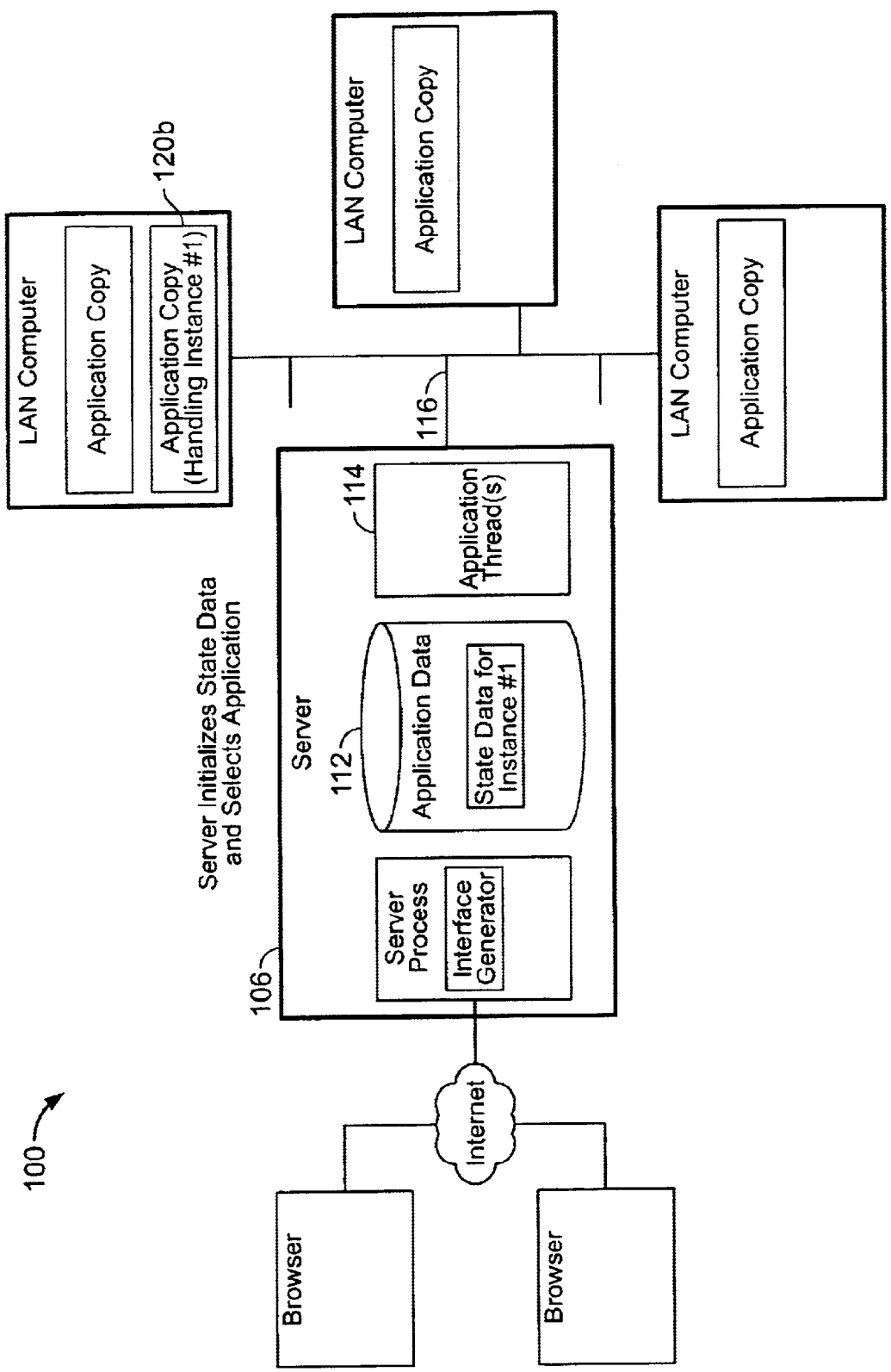
Figure 4:
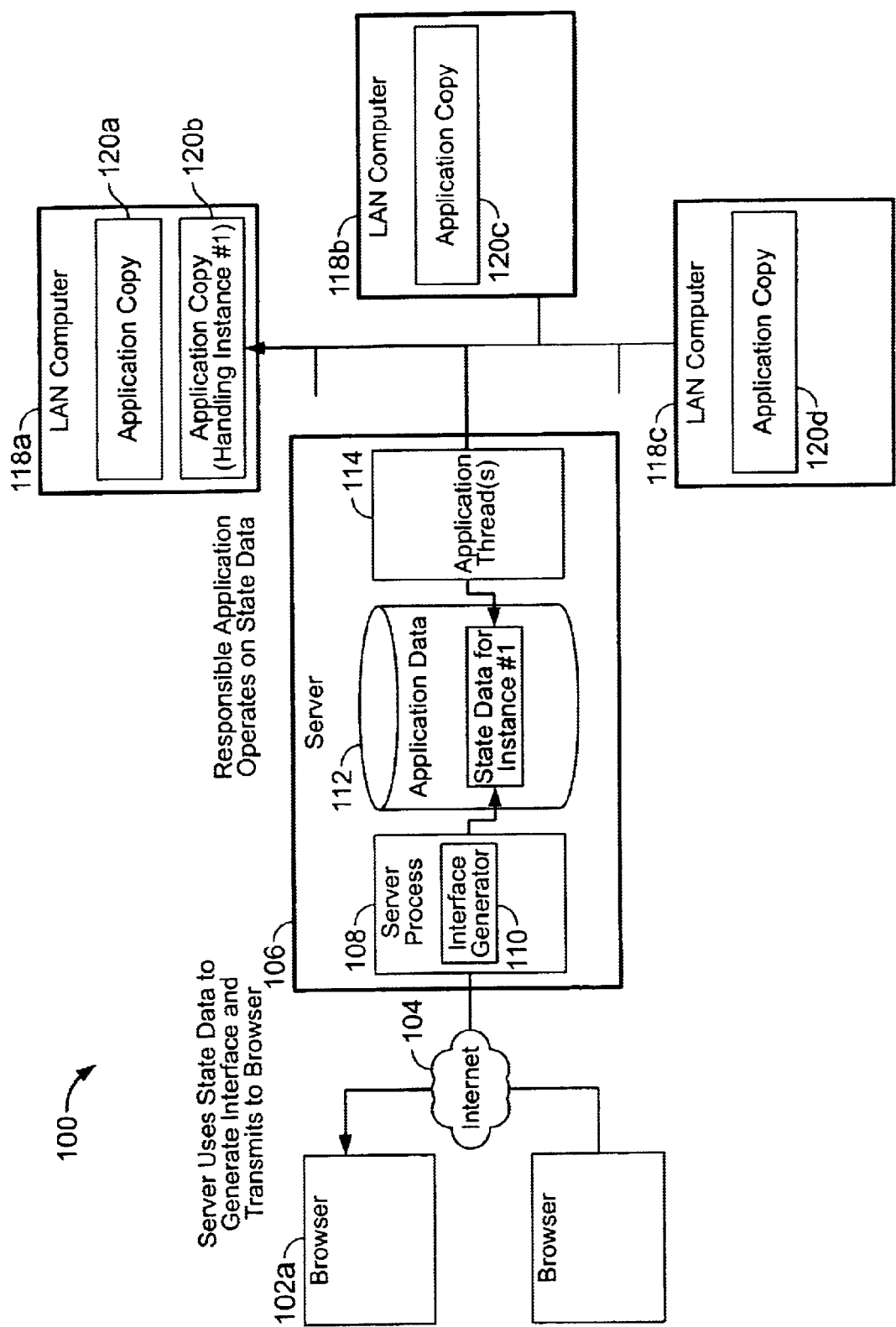

FIGS. 2–4 illustrate operation of the system 100. In FIG. 2, a user navigates browser 102a to the server 106, for example, by specifying the server's URL (Universal Resource Locator) (e.g., www.medicalsimulator.com). In response, as shown in FIG. 3, the server 106 initializes state data 112 for a new application instance. Initializing the state data 112 may include generating an identifier for the instance, for example, an identifier based on the IP (Internet Protocol) address of the user. The server 106 also selects an application 120a–120d to handle the instance. For example, the server 106 may select a particular application 120a–120d based on the current load of the different applications (e.g., load-balance based on how many different instances each application currently handles), the speed of the local area network computer running the application, and so forth.

As shown in FIG. 4, after initialization, communication with the user and execution of the application can proceed independently of one another, for the most part. For example, an application 120b can read and update state data 112 regardless of how frequently the server 106 transmits or receives data from application 120a. Thus, even if a user directs their browser to a different site, the application instance can persist and, potentially, continue. To continue the patient simulation example, even though a user visits a different site to check on stock prices, their patient's ailment will progress. The system does not strictly impose this independence. For example, the server 106 can control the application speed based on the speed of a users connection or how frequently the user interacts with an interface. The server 106 can also store the state data 112 to freeze an application instance for later use.

The server process 108 that handles user interaction can communicate with the "back-end" via the server 106 database 112. For example, the process 108 and application 120b can communicate using a technique known as "handshaking." Thus, a user may interact with an interface control (e.g., a form field on an HTML page) displayed by their browser to send user input to the server 106. The server 106 can write this input into the state data 112 for the user's application instance and set a handshake flag indicating the input requires application 120b processing. After the application 120b finishes its processing it can reset the handshake flag. The interface generator 110 may wait for the application 120b to reset the handshake flag before constructing a new interface.

Figure 5:
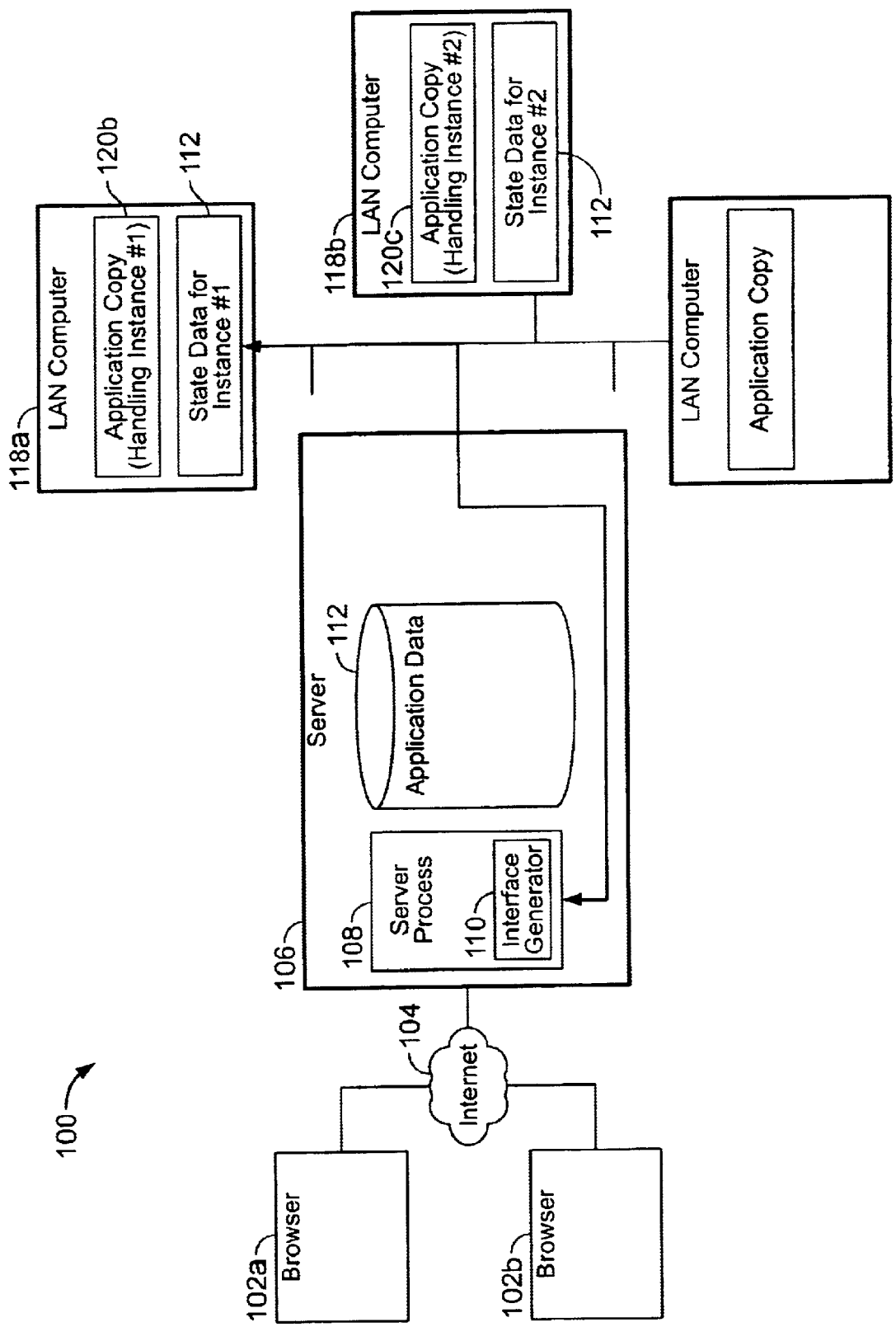

State data 112 may be distributed across different LAN computers 108a–108c instead of residing solely on the server 106. For example, as shown in FIG. 5, each application copy may maintain information for each instance locally. The interface generator 110 can retrieve the state data 112 from the LAN computers when constructing an interface.

C. Client/Server Operation

FIG. 6 shows a flowchart of a server operation 130. As shown, the server identifies 132 different applications running on the LAN computers. For example, the server may run a process or thread that establishes a connection (e.g., a "socket" connection) with each application that announces itself to the server. Though shown in FIG. 6 as initial activity of the server, identifying 132 available applications on the LAN computers can continue over time as different applications and LAN computers go on and off-line.

After receiving 134 a request from a user for an instance of an application, the server 106 selects 136 an application to handle the instance and initializes 138 the state data for that instance. Thereafter, the application can read and/or update the state data, for example, by issuing database commands over an ODBC (Open Database Connectivity) connection. The server also uses the state data to generate interface instructions that control the appearance of the application on a user's browser 142, 144.

The server 106 can construct an interface using a variety of techniques. For example, the interface generator can use PHP (Personal Home Page), ASP (Active Server Page), or CGI (Common Gateway Interface) scripts to dynamically generate HTML or XML (Extensible Markup Language) interface instructions. Typically, these pages will include instructions that read state data for an instance (e.g., by looking up the instance identifier), and, based on the state data values, construct a page of sounds, graphics, and user interface controls. The user interface controls may include "form field" controls and/or a "submit" button that receives user input and transmits 146 this input to the server for processing (e.g., www.medicalsimulator.com? action=CPR). The interface may also include instructions that periodically issue a request to the server 106 for an update.

As shown in FIG. 7, a browser (or other client) receives and processes the generated instructions or data 152 to present the specified pictures, text, or sounds to a user. Though the browser receives discrete sets of web-page instructions, the resulting sequence of displays is nearly indistinguishable from that of an ordinary desktop application. The instructions may also feature applets 154, ActiveX controls, or other programmatic instructions. These instructions can provide fast, direct updating of multimedia elements of an interface. For example, instead of requesting reconstruction of an entire new set of interface instructions, an applet may establish a JDBC (Java Database Connectivity) connection to the data stored on the server 106 and continually replace an image on the interface with a new image. For example, the applet may quickly present a series of images of a patient when the patient's health rapidly improves.

The system 100 described in FIGS. 1–7 can be used to provide a wide variety of applications. For example, the system 100 can be used to provide a simulation of a virtual patient to different users on the Internet.

II. Virtual Patient Simulation

A. User Interface

FIGS. 8–14 show screenshots of a user interface presented by a virtual patient simulator. The simulator provides an interactive, multimedia simulation of a medical examination. The user, acting as a doctor, can examine and interview the virtual patient, track vital signs, enter orders and recommendations, and conduct other simulated activities. Chronic and acute conditions evolve and disappear over time as the virtual patient's health responds to a user's treatments or lack thereof.

The simulator provides extensive medical education and reference information such as pharmacological references (e.g., PDR (Physician's Desk Reference) notes), videos and images illustrating proper use of products and procedures, medical dictionary entries (e.g., from Gray's Anatomy), and links to medical information on the Internet.

The virtual patient and reference information provide an engaging education experience for medical students, medical professionals seeking continuing medical education, and other consumers. The simulation enables users to experiment with different patient treatments and quickly witness the impact of their recommendations on the virtual patient.

Figure 8:
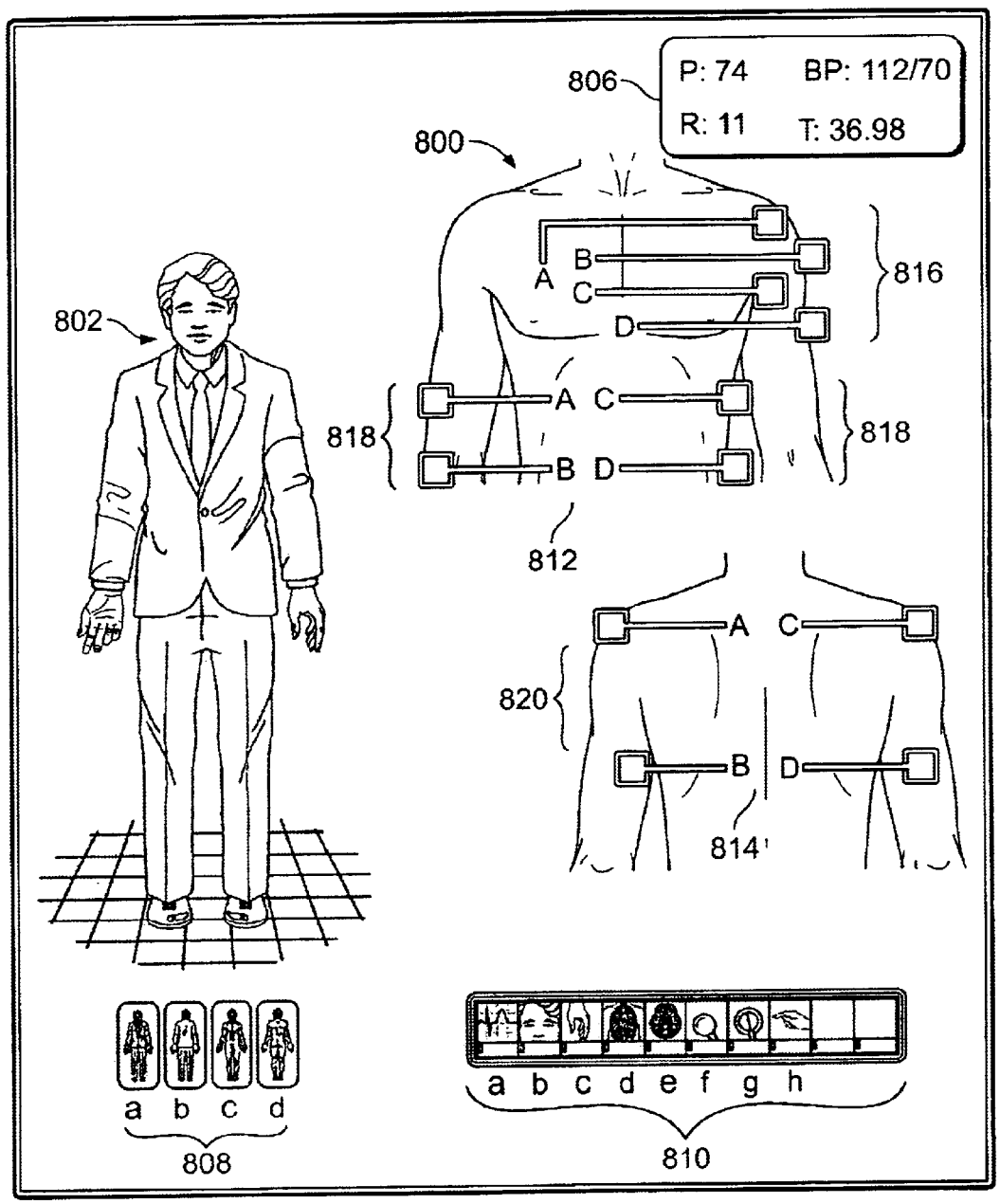

As shown in FIG. 8, a user interface 800 provides a graphic model 802 of a virtual patient. The simulation changes depiction of the model 802 based on the virtual patient's state. For example, the model image may show the hips of the model 802 growing as the virtual patient's weight increases. Similarly, the model's 802 complexion color may sallow due to some illness.

Interface 800 controls 808a–808b enable a user to view both the front and back sides of the virtual patient. Other controls 808c–808d enable the user to select whether the virtual patient model 802 appears clothed or unclothed. The user interface 800 also displays vital statistics 806 such as blood pressure, pulse rate, temperature and so forth.

As shown, the interface 800 provides a palette 810 of controls 810a–810h that correspond to different examination techniques. As shown, the palette 810 includes controls 810a–810h that present a cardiology EKG 810a of the virtual patient, representations of the virtual patient's extremities 810c (e.g., hands and feet), radiology images 810d, microscopy images 810f, and neurological information 810e such as images showing the virtual patient's gait or a "recording" of the virtual patient's voice.

As shown, a user has selected a virtual stethoscope tool 810g from the palette 810. For virtual stethoscope 810g use, the interface 800 presents front 812 and back 814 images of the virtual patient's torso. As shown, the interface 800 also displays "hot spots" 816, 818, and 820. Each hot spot 816a–816d, 818a–818d, 820a–820d maps to a particular location on the virtual patient's torso. Selecting (e.g., using a mouse) one of the hot spots 816a–816d, 818a–818d, 820a–820d simulates placement of a stethoscope on the hot spot and produces corresponding sounds on a computer's audio output (e.g., speakers). Just as in a real-life medical exam, use of the virtual stethoscope can identify breathing or cardiac abnormalities. For example, using the virtual stethoscope to listen at hot spots 816a–816d produces sounds of the virtual patient's heart. More particularly, hot spot 816a corresponds to the second right intercostal space. Thus, selecting hot spot 816a causes the simulator to produce sounds corresponding the virtual patient's aortic valve. Other hot spots "listen" to other bodily functions. For example, hot spots 818a–818d correspond to the virtual patient's renal arteries while hot spots 820a–820d correspond to the virtual patient's lungs. The sounds produced vary according to the state of the virtual patient. That is, the cardiac rhythms presented by the simulator can depend on the blood pressure, pulse, and age of the virtual patient.

Instead of "listening" to the virtual patient using the virtual stethoscope 810g, a user may choose to virtually percuss (i.e., simulate a gentle thumping of a patient's body) the virtual patient. Medical professionals often use percussion to identify abnormal masses. Selecting the percussion tool 810h may display a different collection of hot spots than those shown in FIG. 8. Selecting one of the hot spots causes the simulator to produce sounds corresponding to percussion of the corresponding area. Again, the sounds produced depend on the state of the virtual patient. For example, percussion of a healthy virtual patient's abdomen often produces a resonant echo while percussion of the abdomen of a virtual patient having a swollen liver may sound flatter.

Figure 9:
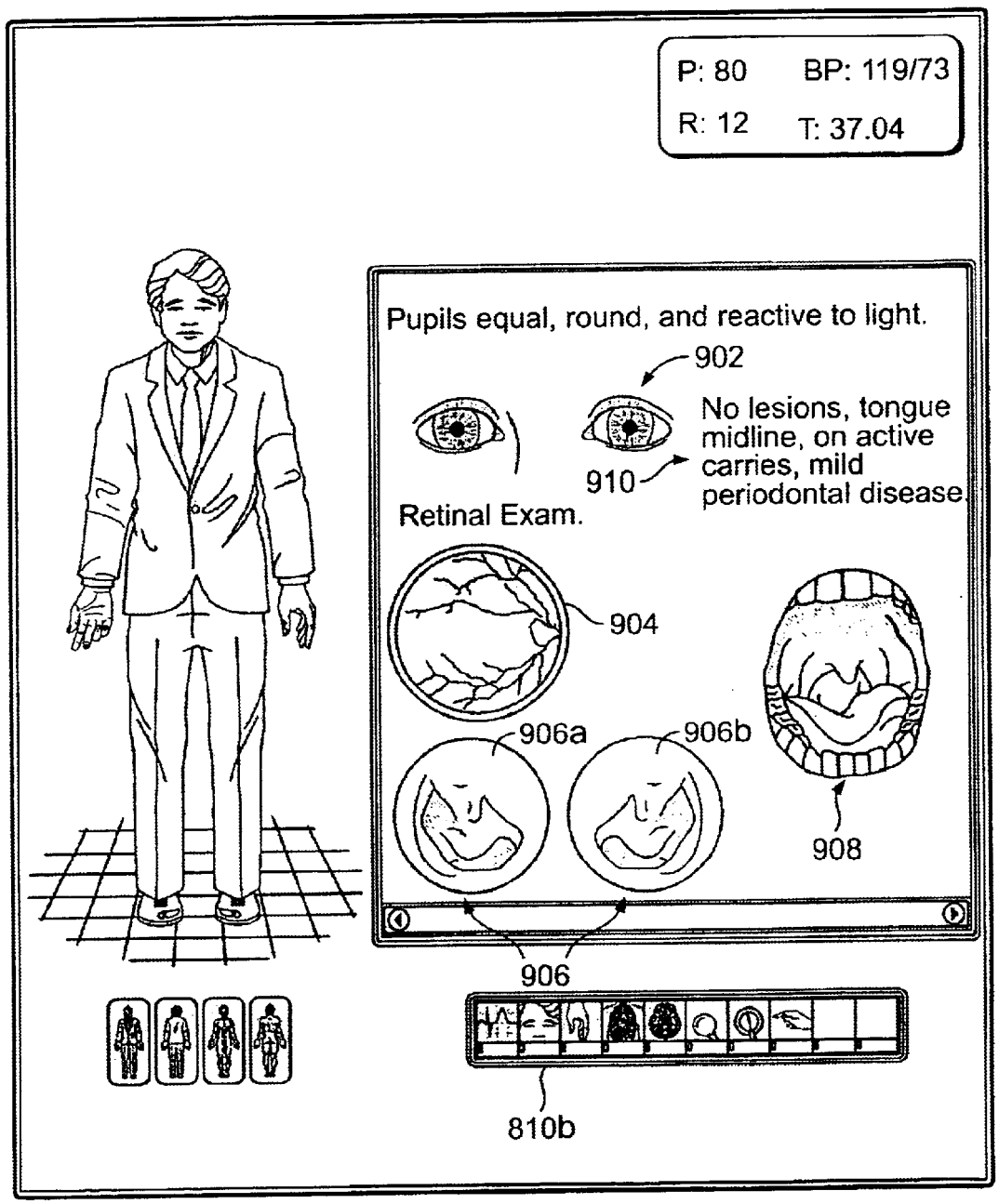

As shown in FIG. 9, the interface palette also includes a fundascope/odoscope tool 810b for viewing images of the virtual patients eyes 902, retina 904, ears 906a–906b, nose (not shown), and throat 908. Descriptions 910 may accompany these images. Again, the virtual patient images 902–908 are not the same for each virtual patient, but are instead based on the virtual patient's current health. For example, a virtual patient suffering from retinopathy may cause display of a retinal image 904 depicting strands of white fibrous tissue? Similarly, a virtual patient suffering from an inner ear infection may cause display of an ear image 906a–906b depicting a reddened tympanic membrane.

Figure 10:
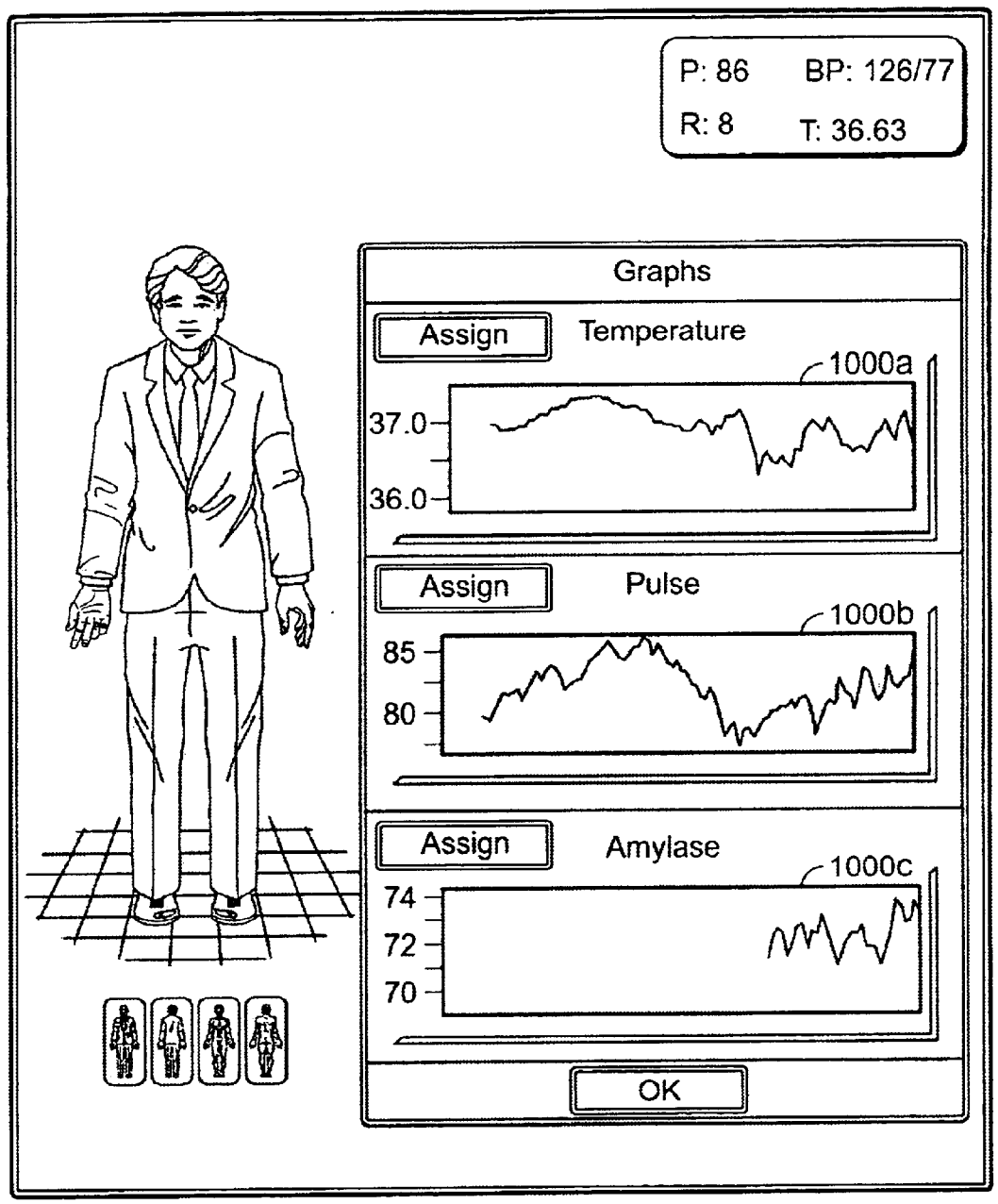

As shown in FIG. 10, a user can view graphs 1000 of a virtual patient's vital statistics and lab tests over time. The graphs 1000 enable the user to quickly grasp the effects their treatment has had on the virtual patient and identify correlations between movements of different charted variables.

Figure 11:
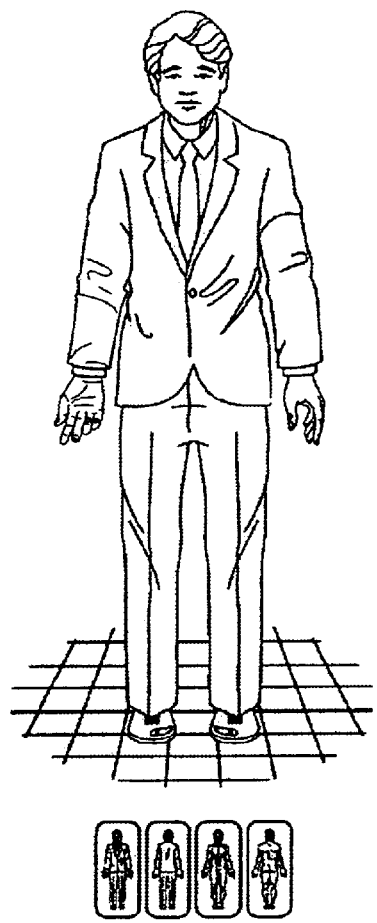

As shown in FIG. 11, the simulator provides each virtual patient with a patient history 1100. The history 1100 may include clues to potential ailments. The history 1100 also may chronicle changes in the virtual patient's health over time.

Figure 12:
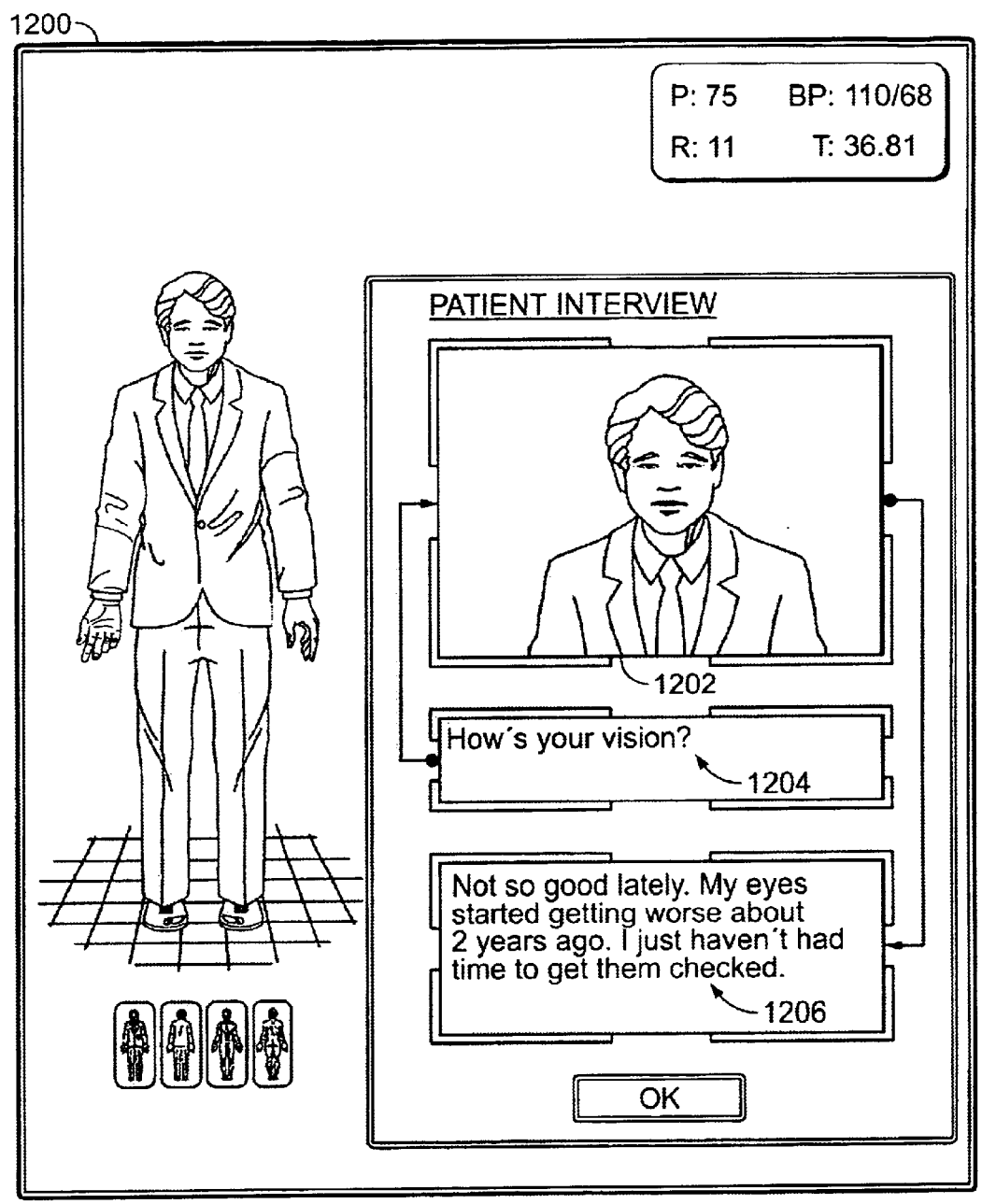

As shown in FIG. 12, the interface 1200 enables a user to ask the virtual patient a question, for example, by typing questions into a text field 1204. Just as in real-life, questioning a patient can quickly yield information needed to formulate and confirm a diagnosis. The simulator generates a virtual patient response 1206 for each question asked 1204. Additionally, the simulator can adjust the facial expression 1202 of the virtual patient to portray a patient's emotional response to a question 1204. Potentially, the virtual patient's expression 1202 may be as telling as their actual response. As shown, the questions 1204 and answers 1206 take the form of text, however, in other embodiments, speech recognition and speech synthesis handle question input and answer output. Again, the response of the virtual patient can depend on state data. For example, the patient's response to "How's your vision" can differ for a healthy patient and a patient suffering from diabetes.

Figure 13:
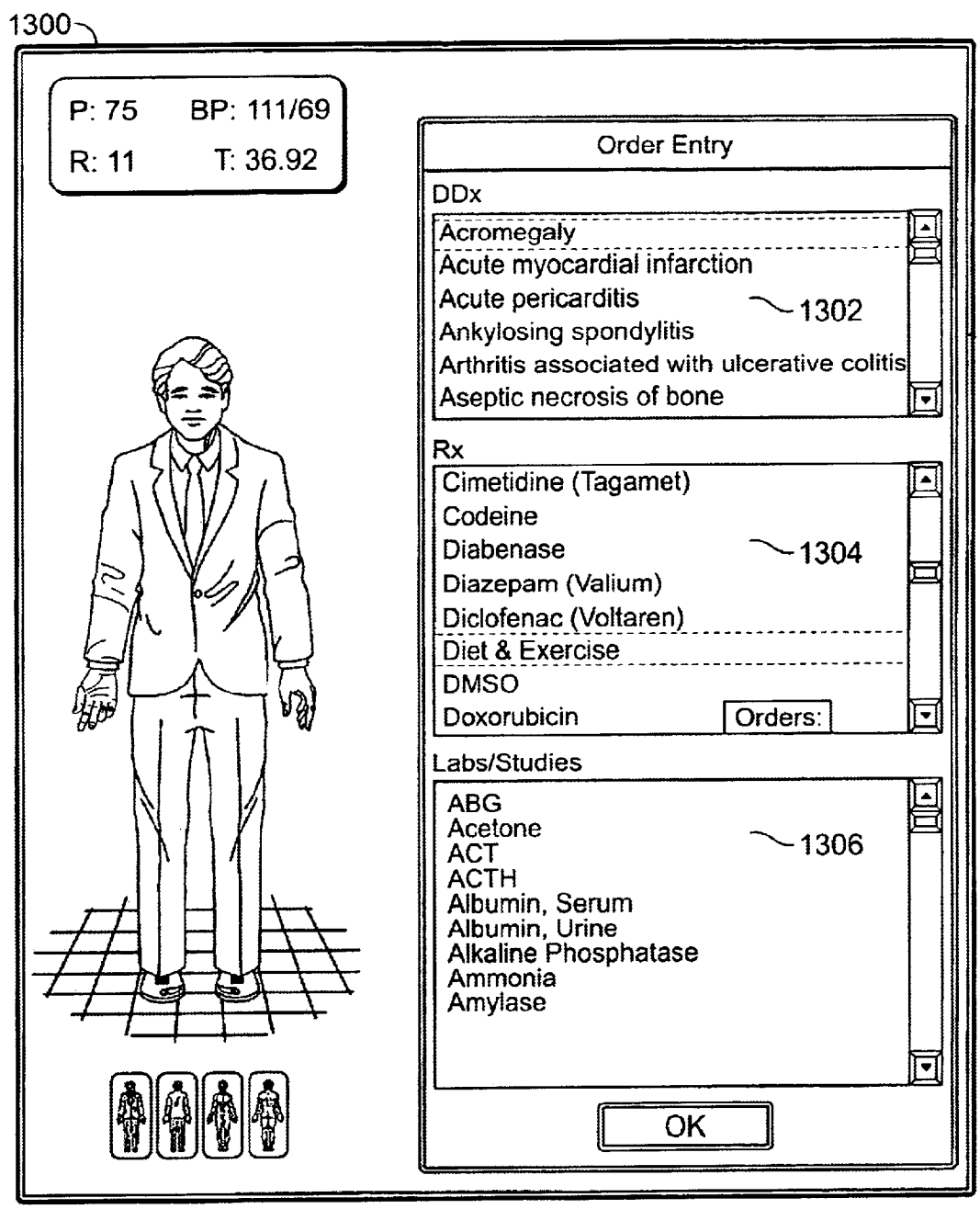

As shown in FIG. 13, the interface 1300 enables a user to make different interventions. For example, the user can make a diagnosis 1302. The simulator may provide feedback when a user correctly diagnoses a virtual patient ailment. The user may also order different lab tests 1306. The simulator returns lab results based on state data of the virtual patient. The lab results can provide clues to ailments afflicting the virtual patient.

A user may also prescribe an over-the-counter or prescription medication 1304 or order a lifestyle change such as a change in diet. Such interventions can alter the state of the virtual patient. Of course, as in real-life, such interventions can have beneficial and/or problematic results and can cause predictable and unpredictable side-effects.

Figure 14:
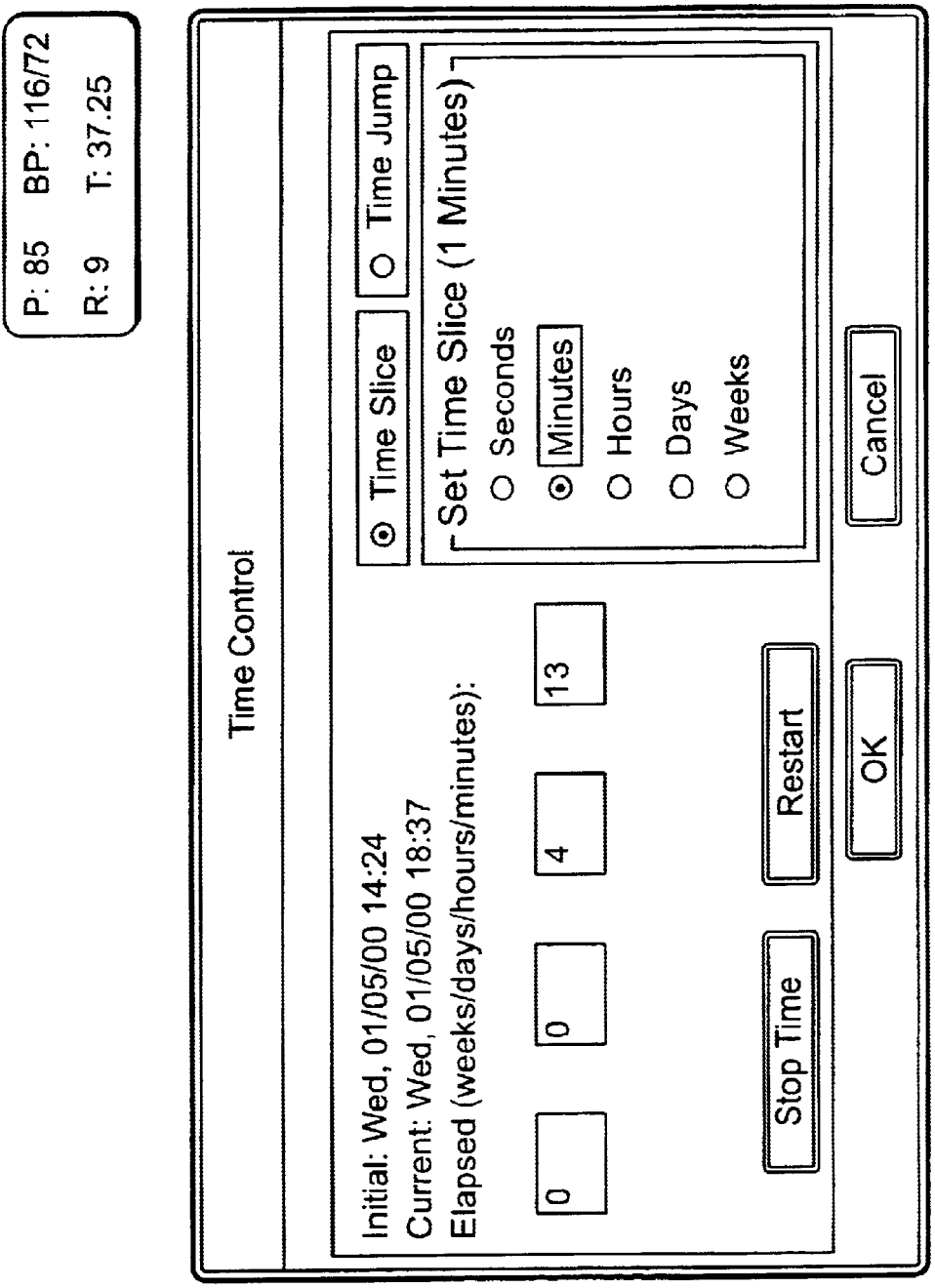

As shown in FIG. 14, the interface permits users to control "virtual time". That is, a user can speed up the simulation to see a long-term illness unfold in a matter of minutes or slow down the simulation to see a quick-striking illness slowly unfold.

FIGS. 8–14 illustrate an interface that provides users with techniques for monitoring and treating a virtual patient. The screenshots shown, however, are merely an example of one possible interface. A wide variety of other user interface presentations can take advantage of the techniques described herein.

B. Multimedia Presentation of a Virtual Patient

FIGS. 15A–15B show data structures 1502–1538 that control multimedia presentations provided by the interface. For example, the "Patient Views" data structure defines different patent model images. The multimedia fields MMFile1, MMFile2, MMFile3, and MMFile4 of the "Patient Views" data structure specify the file locations of previously generated model images corresponding to clothed-front-side, clothed-back-side, unclothed-front-side, and unclothed-back-side model views, respectively. These images correspond to controls 808*a*–808*d* in FIG. 8. Changing the files referred to can change the presentation of the virtual patient. For example, changing the file associated with MMFile1 from aprime.jpg to slim_prime.jpg can cause the user interface to present a slimmer clothed-front-side image of the virtual patient.

Similarly, the Chest "Front Auscultation" data structure 1510 defines multimedia presentations for use of the virtual stethoscope (see FIG. 8). Data structure elements Sound1, Sound2, Sound3, and Sound4 correspond to the sounds produced by selecting hot spots 816 in FIG. 8. Again, changing the sound files associated with Sound1, Sound2, Sound3, or Sound4 change the sound file played.

As shown, the data structures specify multimedia presentations for front auscultation 1506 and percussion 1508 of the virtual patient's abdomen, front 1510 and back 1512 auscultation of the virtual patient's chest, and percussion of the virtual patient's back 1514. The data structures also specify multimedia presentations for a virtual patient EKG 1516, examination of extremities 1518–1522, examination of head, eyes, ears, nose, and throat 1524–1530, neurological examination such as speech 1532 and gait 1534, and radiology images of the virtual patient's chest 1536 and skull 1538.

Though the data structures listed in FIGS. 15A and 15B include the term "objects", the data structures need not be implemented using an object-oriented methodology.

C. Generating a Virtual Patient

In some embodiments, the simulator operates by interpreting data structures encoding different virtual patient characteristics. For example, a developer can code data structures that define the progression of different medical conditions. Procedures interpret the data structures to present a virtual patient. Interpretation of the data structures can include accessing and modifying virtual patient state data. Such state data can include vital statistic variables (e.g., pulse rate, age, gender, weight, systolic blood pressure, diastolic blood pressure, respiration, and temperature), laboratory test variables, the state of different conditions, and other developer defined variables.

With some exceptions, described below, different virtual patient characteristics can proceed independently of one another. For example, different medical conditions may read and update the state data of the virtual patient and act without knowledge of other conditions. Thus, a virtual patient can suffer from a strange mix of symptoms caused by different conditions. To successfully treat the patient, the user learns to untangle the different symptoms into individual, treatable illnesses.

FIG. 16 shows a process 1600 for providing a virtual patient. Initially, a developer defines 1602 a domain of potential virtual patient characteristics. For example, the developer can define data structures for different ailments that evolve over time ("evolutions") that are computed by mathematical modeling of other variables ("computations"), for random fluctuations in variables ("migrations"), and for different treatments (e.g., drugs) a user can prescribe.

A patient generation process generates 1604 a virtual patient by selecting virtual patient characteristics from the domain of potential virtual domain characteristics. For example, the patient generator process 1604 may generate one patient that has the potential for diabetes and may later generate another patent that has the potential for osteoporosis. Patients are not limited to a single characteristic but can instead have different mixes of potential ailments.

Patient generation 1604 may feature interpretation of a patient generation script that specifies different probabilities of virtual patient characteristics occurring in the virtual patient. Patient generation 1604 may also initialize variables to specific values. The script may identify a particular medical area. For example, a script that generates a virtual patient having osteoporosis and cataracts may belong to a "geriatric" medical area. Additionally, the script may differ for men and women.

The script used to generate a patient may be randomly selected from all scripts. Alternatively, a user may specify a medical area and restrict patient generation to those scripts belonging to that area. Patient generation 1604, however, can occur without a script. For example, a patient generator can produce a virtual patient having a random selection of medical characteristics.

After generating 1604 the virtual patient, a simulator presents 1606 the virtual patient to the user based on virtual patient state data (e.g., vital statistic variables and lab test variables) and updates 1608 the state data by interpreting the data structures defining virtual patient characteristics.

FIG. 17 shows a diagram of a simulator 1700. In addition to the user interface 1722 (see FIGS. 8–14), the simulator 1700 includes procedures 1701 that interpret data structures defining the virtual patient. The procedures 1701 handle questioning 1702 of the virtual patient (e.g., review of systems (ROS) questions), responding to lab test 1704 requests from the user, responding to physical examinations 1706 requested by the user, and responding to orders 1708 issued by the user.

The procedures 1701 also modify state data of the virtual patient by interpreting evolution 1712 and migration 1714 data structures, and computation 1715 data structures. Evolutions 1712 control variables to reflect some condition. For example, a diabetes evolution will cause the virtual patient to gain weight. By contrast, migrations 1714 randomly vary variables within specified bounds. The combination of migrations 1714 and evolutions 1712 force a user to distinguish between significant and insignificant variations in vital signs and lab tests results. Computations 1715 allow mathematical modeling of system variables based on value(s) of other system variable(s).

As shown, the simulator 1700 also provides multimedia files 1716 such as video (e.g., MPEG (Motion Pictures Experts Group)) files, sound files, and picture (e.g., JPEG (Joint Photographers Experts Group)) files. These files may include instructional references material and/or multimedia features used to present the virtual patient. The state data 1718 can include references or copies of the multimedia files that reflect the current state of the patient (see FIGS. 15a and 15b).

Trigger and morphing procedures 1710 can update the multimedia files associated with the virtual patient based on logic operating on variables. For example, a trigger 1710 procedure may change an image of a patient's torso from "normal_torso.jpeg" to "slim_torso.jpeg" if the patient's weight falls under one-hundred fifty pounds.

FIG. 18 depicts evolution 1800 of a medical condition. Evolutions alter variable values and/or lab test results to reflect some condition. The evolution 1800 has several modes: an initial mode 1802 before any events (e.g., treatments by the user and/or other state data) initiate the evolution, an interim mode 1808 when the evolution temporarily lies dormant, and an active mode 1814 when the evolution changes 1818 the virtual patient's state data.

In addition to programming different events or criteria that start an evolution 1804 and the state data affected by an active 1814 condition, a programmer can identify different inhibiting events or criteria 1806, 1810 that halt progression of the evolution. For example, an order for "diet and exercise" may halt many different illnesses. Thus, identification of disease warning signs and prompt treatment can prevent the onset of a disease.

A programmer can also control the dominance 1816 of an evolution over other evolutions. For example, a first evolution may elevate blood pressure while a second evolution decreases blood pressure. If so desired, a programmer can code the first evolution to cancel the second evolution.

FIG. 19 shows a listing of statements defining an evolution 1900 for "Diet and Exercise". Such an evolution can regulate vital signs in a manner beneficial to a virtual patient's health. The evolution 1900 begins when a user orders "Diet and Exercise". After an interim period of four days 1906, the evolution begins decreasing a virtual patient's weight 1910a and glucose levels 1910b–1910d. While nothing can inhibit 1908 the effects of exercise, the evolution 1900, as shown, does not directly cancel any other evolutions 1908. While recommending "Diet and Exercise" does not directly cancel other evolutions, the evolution's 1900 control over weight and glucose variable values may inhibit a disease triggered by a particular weight or glucose level.

FIG. 20 shows a listing of statements that define a migration. Like an evolution, a migration adjusts the values of variables and other state data. Unlike an evolution the migration adjusts the state data in a more random manner to represent ordinary fluctuations in measurements. As shown, the "Activated clotting time" migration maintains the value 2002 of the corresponding "ACT" variable between "114" and "186" from a starting point of "143". The migration operates once a "virtual" minute 2004. The migration is not purely random, but instead implements a "random walk" having changes that amount to, in this case, a 4% increase or decrease 2006 at most.

FIG. 21 shows a process 2100 for producing a trigger. Triggers implement conditional statements. Triggers can not affect variables but rather affect multimedia or text objects based on the values of variables. Typically, a programmer can use triggers to substitute different multimedia presentations of a virtual patient based on satisfaction of some criteria. As shown, the process 2100 tests for satisfaction of some criteria 2102. For example, the trigger may test the variables and/or the issuance of some order by the user (e.g., prescribing a drug). If satisfied, a trigger makes a specified alteration 2104.

FIG. 22 shows data structure statements 2202 that define the sounds associated with virtual percussion of the back of the virtual patient. Each sound corresponds to one of the hot spots (see FIG. 7). A trigger 2204 can change the sound of one of the hot spots. As shown, the trigger substitutes references to Wav Files/Percussion/percussThin.wav for the previous value of Sound1 ("PercusResonant.wav") if the weight of the patient falls between "100" and "120" pounds.

Like triggers, morphing can alter the image used to portray the virtual patient. FIG. 23 shows a flowchart 2300 of a process for morphing an image of a patient. Based on a specified maximum and minimum variable value, the process 2300 uses a current value of a variable to determine an offset into a video file, such as a file slowly morphing the image of a virtual patient from a slim to heavyset appearance. The process presents the image corresponding to the offset. The video file provides a fine gradation of images thus can present smooth and gradual changes in the virtual patient.

FIG. 24 shows a listing of statements defining a morph. The "weight" morph is based on the weight variable and extends from a minimum weight of 164 to a maximum weight of 184. Thus, if a patient weights "174", the corresponding offset would index halfway through a video file and present the corresponding image.

FIG. 25 shows a flowchart of a process 2500 that provides virtual patient responses to different questions posed by the user (see FIG. 12). After receiving a question 2502, the process searches 2502 for a corresponding entry in a collection of questions. For example, the process may identify key words in the question by eliminating articles and prepositions and search for a stored question having the identified key words. The keywords may also include Boolean criteria (e.g., this is the response when the query includes word a AND word b but NOT word c. The process 2500 may alternatively use other natural language processing techniques to match a user's question with a particular response. After finding an entry, the process presents 2506 the response corresponding to the question.

FIG. 26 shows a listing of statements used to define a "Review of Systems" response. The statements include a question, answer, keywords identifying the entry, an entry for the log, and a facial expression.

FIGS. 27–29 show data structures for lab tests, user orders, and physical examinations, respectively. FIG. 30 shows a data structure for a computation, where the MethodName "ComputeBPDiastolic" refers to a compiled function in a DLL.

A computation enables the simulator to use complex mathematical models of a virtual patient. The computation enables a programmer to specify condition statements (e.g., if (temperature>100)) and/or relationships between variables (e.g., systolic pressure=diastolic pressure).

All components of the virtual patient simulator may reside on the same computer. In other embodiments, the virtual patient simulator uses the architecture shown in FIGS. 1 to 7 to provide different Internet users with a simulation of a patient medical exam.

Briefly, the simulator procedures 120 operate on different state data and different data structures for different virtual patients. Each virtual patient has an entry in a patient table 3110. Each virtual patient can correspond to a single application instance, though many different clients can simultaneously engage the same patient for group treatment, discussion, and education. A patient identifier may key each patient table entry 3110.

As shown the database 106 includes tables that track the current loads 3112 of different LAN virtual patient simulators, vital statistic variables 3120, lab variables 3126, pending physician orders 3116 and questions 3118 and their corresponding responses 3122, 3124. The database 106 can also store the data structures identifying the images and sounds 2904 that portray the virtual patient's current health.

Embodiments

The techniques described here are not limited to any particular hardware or software configuration; they may find applicability in any computing or processing environment. The techniques may be implemented in hardware or software, or a combination of the two. Preferably, the techniques are implemented in computer programs executing on programmable computers that each include a processor, a storage medium readable by the processor (including volatile and non-volatile memory and/or storage elements), at least one input device, and one or more output devices. Program code is applied to data entered using the input device to perform the functions described and to generate output information. The output information is applied to one or more output devices.

Each program is preferably implemented in a high level procedural or object oriented programming language to communicate with a computer system. However, the programs can be implemented in assembly or machine language, if desired. In any case, the language may be a compiled or interpreted language.

Each such computer program is preferable stored on a storage medium or device (e.g., CD-ROM, hard disk or magnetic diskette) that is readable by a general or special purpose programmable computer for configuring and operating the computer when the storage medium or device is read by the computer to perform the procedures described in this document. The system may also be considered to be implemented as a computer-readable storage medium, configured with a computer program, where the storage medium so configured causes a computer to operate in a specific and predefined manner.

Other embodiments are within the scope of the following claims.

What is claimed is:

1. A method of simulating an encounter with a virtual patient, the method comprising:

displaying an image of the virtual patient;

receiving user selection of an area of the image of the virtual patient; and transmitting signals that correspond to the user selected area of the image, the signals being based on the state of the virtual patient, the signals comprise data corresponding to percussion sounds from percussing the virtual patient.

2. The method of claim 1, wherein the image comprises an image of a torso.

3. The method of claim 1, further comprising providing one or more hot spots anchored to preselected areas of the image; and wherein receiving user selection of an area comprises receiving user selection of one of the one or more hot spots.

4. The method of claim 1, wherein transmitting signals comprises playing a sound file.

5. The method of claim 1, wherein the state of the virtual patient comprises one or more of the following: an age, a gender, a blood pressure, and a weight.

6. A computer program product, disposed on a computer readable medium, for simulating an encounter with a virtual patient, the program comprising instructions for causing a computer to:

display an image of the virtual patient;

receive user selection of an area of the image of the virtual patient;

transmit signals that correspond to the user selected area of the image, the signals being based on the state of the virtual patient, the signals comprise data corresponding to percussion sounds from percussing the virtual patient.

7. The computer program of claim 6, wherein the image comprises an image of a torso.

8. The computer program of claim 6, further comprising instructions that display one or more hot spots anchored to preselected areas of the image; and wherein the instructions that receive user selection of an area comprise instructions that receive user selection of one of the one or more hot spots.

9. The computer program of claim 6, wherein the instructions that transmit signals comprise instructions that play a sound file.

10. The computer program of claim 6 wherein the state of the virtual patient comprises one or more of the following: an age, a gender, a blood pressure, and a weight.

* * * * *